US011274292B2

(12) United States Patent
Suh et al.

(10) Patent No.: US 11,274,292 B2
(45) Date of Patent: *Mar. 15, 2022

(54) DEVICES AND METHODS FOR PLASMID PURIFICATION

(71) Applicant: PHYNEXUS, INC., San Jose, CA (US)

(72) Inventors: Chris Suh, San Jose, CA (US); Carrie Loan Kim Huynh, San Jose, CA (US); Lee Hoang, Santa Clara, CA (US); Douglas T. Gjerde, Saratoga, CA (US); Jonathan Michael Grambow, San Francisco, CA (US)

(73) Assignee: PHYNEXUS, INC., San Jose, CA (US)

( * ) Notice: Subject to any disclaimer, the term of this patent is extended or adjusted under 35 U.S.C. 154(b) by 1017 days.

This patent is subject to a terminal disclaimer.

(21) Appl. No.: 15/585,109

(22) Filed: May 2, 2017

(65) Prior Publication Data

US 2017/0233721 A1   Aug. 17, 2017
US 2020/0056168 A9   Feb. 20, 2020

Related U.S. Application Data

(63) Continuation-in-part of application No. 15/482,778, filed on Apr. 9, 2017, now Pat. No. 10,883,100, which is a continuation-in-part of application No. 15/290,847, filed on Oct. 11, 2016, now Pat. No. 10,597,652, which is a continuation-in-part of application No. 14/585,070, filed on Dec. 29, 2014, now abandoned, which is a continuation-in-part of application No. 13/434,656, filed on Mar. 29, 2012, now Pat. No. 8,921,539, which is a continuation-in-part of application No. PCT/US2011/030232, filed on Mar. 29, 2011.

(51) Int. Cl.
| | | |
|---|---|---|
| *C12N 15/10* | (2006.01) | |
| *G01N 35/10* | (2006.01) | |
| *B01D 15/42* | (2006.01) | |
| *B01D 15/12* | (2006.01) | |
| *C12Q 1/6806* | (2018.01) | |
| *B01D 15/20* | (2006.01) | |
| *G01N 35/00* | (2006.01) | |
| *B01D 15/32* | (2006.01) | |
| *B01D 15/36* | (2006.01) | |

(52) U.S. Cl.
CPC ....... *C12N 15/1017* (2013.01); *B01D 15/125* (2013.01); *B01D 15/203* (2013.01); *B01D 15/424* (2013.01); *C12N 15/101* (2013.01); *C12N 15/1003* (2013.01); *C12Q 1/6806* (2013.01); *G01N 35/10* (2013.01); *B01D 15/322* (2013.01); *B01D 15/363* (2013.01); *G01N 2035/00475* (2013.01)

(58) Field of Classification Search
None
See application file for complete search history.

(56) References Cited

U.S. PATENT DOCUMENTS

| | | | |
|---|---|---|---|
| 5,217,593 A * | 6/1993 | MacConnell | G01N 27/4473 204/457 |
| 5,330,914 A | 7/1994 | Uhlen et al. | |
| 5,395,521 A | 3/1995 | Jagadeeswaran | |
| 5,556,598 A | 9/1996 | Raybuck et al. | |
| 5,561,064 A | 10/1996 | Marquet et al. | |
| 5,833,927 A | 11/1998 | Raybuck et al. | |
| 6,194,562 B1 | 2/2001 | Smith et al. | |
| 6,274,371 B1 * | 8/2001 | Colpan | C12N 15/101 435/259 |
| 6,942,802 B2 | 9/2005 | Sundberg et al. | |
| 7,482,169 B2 | 1/2009 | Gjerde et al. | |
| 7,488,603 B2 | 2/2009 | Gjerde et al. | |
| 7,935,505 B2 | 5/2011 | Blattner et al. | |
| 8,053,247 B2 | 11/2011 | Feuerstein et al. | |
| 8,377,715 B2 | 2/2013 | Suh et al. | |
| 2002/0001836 A1 | 1/2002 | Leonard | |
| 2004/0076980 A1 | 4/2004 | Charlton et al. | |
| 2005/0112753 A1 | 5/2005 | Antoniou | |
| 2006/0078923 A1 | 4/2006 | McKernan et al. | |
| 2006/0105391 A1 | 5/2006 | Engel et al. | |
| 2006/0177354 A1 | 8/2006 | Daf | |
| 2006/0191893 A1 | 8/2006 | Weinfield et al. | |
| 2007/0117090 A1 | 5/2007 | Charlton | |
| 2007/0142623 A1 | 6/2007 | Hesketh et al. | |
| 2008/0020446 A1 | 1/2008 | Jia | |
| 2008/0039619 A1 | 2/2008 | Singer | |

(Continued)

FOREIGN PATENT DOCUMENTS

WO   WO-2007/115046 A1   10/2007

OTHER PUBLICATIONS

Qiagen: Qiafilter Plasmid Purification Handbook, Apr. 2012, 44 pages. (Year: 2012).*
Kachel et al. High-throughput isolation of ultra-pure plasmid DNA by a robotic system. BMC Biotechnology 6:9 (9 pages); Feb. 16, 2006. (Year: 2006).*
Qiagen Plasmid Mini Handbook. (Year: 1999).*
U.S. Notice of Allowance dated Nov. 12, 2019 in corresponding U.S. Appl. No. 15/290,847.
Harris et al., "High-Speed Plasmid Isolation Using 96-Well, Size-Exclusion Filter Plates", BioTechniques, 32:626-631 (Year: 2002).
Office Action dated May 8, 2019 for corresponding U.S. Appl. No. 15/290,847.
Itoh et al. "Automated Filtration-Based High-Throughput Plasmid Preparation System" Genome Research 9:463-470 (Year: 1999).

(Continued)

*Primary Examiner* — Samuel C Woolwine
(74) *Attorney, Agent, or Firm* — Harness, Dickey & Pierce, P.L.C.

(57) ABSTRACT

The invention provides columns (including pipette tip columns) and automated methods for the purification of nucleic acids including plasmids. Nucleic acids can be purified from unclarified, clarified or partially-clarified cell lysates that contain cell debris. The columns typically include a bed of medium positioned above a bottom frit and with an optional top frit. Plasmid preparation scales include miniprep, midiprep, maxiprep, megaprep and gigaprep.

18 Claims, 7 Drawing Sheets

(56) References Cited

U.S. PATENT DOCUMENTS

| | | | |
|---|---|---|---|
| 2008/0118525 A1* | 5/2008 | Donini | A61P 31/14 424/185.1 |
| 2008/0206746 A1 | 8/2008 | Jia | |
| 2008/0299621 A1 | 12/2008 | Tatnell et al. | |
| 2008/0300397 A1 | 12/2008 | Kenrick et al. | |
| 2009/0004716 A1 | 1/2009 | Draghia-Akli et al. | |
| 2011/0117641 A1 | 5/2011 | Jia | |
| 2011/0294205 A1 | 12/2011 | Hukari et al. | |
| 2012/0252115 A1 | 10/2012 | Suh et al. | |
| 2014/0134708 A1 | 5/2014 | Shaw et al. | |
| 2014/0134718 A1 | 5/2014 | Hiesinger et al. | |
| 2015/0119563 A1* | 4/2015 | Suh | C12N 15/101 536/25.4 |
| 2016/0355827 A1 | 12/2016 | Williams et al. | |

OTHER PUBLICATIONS

Office Action dated May 30, 2019 in corresponding U.S. Appl. No. 15/482,778.

Office Action dated Oct. 15, 2018 for corresponding U.S. Appl. No. 15/290,847.

Lorenz, M. "Liquid-Handling Robotic Workstations for Functional Genomics", Journal of the Association for Laboratory Automation 9(4): p. 262-267, Aug. 2004.

U.S. Office Action dated Nov. 28, 2017 in corresponding U.S. Appl. No. 14/585,070.

U.S. Office Action dated Mar. 20, 2017 in corresponding U.S. Appl. No. 14/585,070.

U.S. Notice of Allowance dated Aug. 25, 2014 in corresponding U.S. Appl. No. 13/434,656.

U.S. Office Action dated Mar. 11, 2014 in corresponding U.S. Appl. No. 13/434,656.

Non-Final Office Action dated Mar. 31, 2020 issued in U.S. Appl. No. 15/482,778.

Notice of Allowance dated Aug. 26, 2020 in U.S. Appl. No. 15/482,778.

U.S. Office Action dated Dec. 20, 2019 in corresponding U.S. Appl. No. 15/482,778.

Qiagen Plasmid Purification Handbook, Third Edition, 52 pages, (2005).

* cited by examiner

DEVICES AND METHODS FOR PLASMID PURIFICATION

CROSS-REFERENCE TO RELATED APPLICATIONS

This is a continuation in part of U.S. patent application Ser. No. 15/482,778, filed Apr. 9, 2017, which is a continuation in part of U.S. patent application Ser. No. 15/290,847, filed Oct. 11, 2016, which is a continuation in part of US Patent Application Ser. No. 14/585,070, filed Dec. 29, 2014, which is a continuation in part of U.S. patent application Ser. No. 13/434,656, filed Mar. 29, 2012, which is a continuation in part of International Application No. PCT/US11/30232, filed Mar. 29, 2011.

FIELD OF THE INVENTION

This invention relates to methods and devices for sample preparation, such as separating (i.e., extracting or purifying) nucleic acids such as DNA and RNA, including circular self-replicating elements such as plasmids, BACs, YACs, cosmids, fosmids and bacteriophage vectors such as M13. Pipette tip columns are used to purify nucleic acids from tissues, unclarified cell lysates or other samples containing particulates and cell debris. Nucleic acids purified by methods of the invention are essentially endotoxin-free, making suitable for mammalian transfection and transformation. Depending on the scale of the preparation, up to 15 mg of plasmid DNA can be obtained in an automated fashion.

BACKGROUND OF THE INVENTION

Commercially-available formats for nucleic acid purification include spin columns, magnetic beads in a tube, gravity or vacuum to draw liquids through a column or plate. In these formats, nucleic acids are isolated as follows. The cells are grown in a suitable medium, the culture is centrifuged to collect the cells and the growth medium is discarded. Next, the cells are lysed to release the nucleic acids. Usually, a second centrifugation step is performed after lysis to pellet the cell debris and produce a clarified lysate. The nucleic acids are then purified from the clarified lysate.

When the spin column format is employed, several additional centrifugations are performed. Because these methods require at least two centrifugation steps, they are time-consuming, laborious and difficult to fully automate. Spin column methods require significant human intervention and cannot be performed in a walk-away fashion. Therefore, there exists a need for more automated methods of plasmid and nucleic acid preparation.

Furthermore, plasmids purified by existing commercially-available methods often contain significant amounts of endotoxin, making them unsuitable for transfection. Therefore, there exists a need for automated, high-throughput nucleic acid purification. Pipette tip columns can be used to meet this need. Additionally, there exists a need for purifying nucleic acids from unclarified cell lysates and other samples containing particulates and cell debris. For plasmid purification, there is a need for endotoxin-free plasmid.

Additionally, there exists a need for large-scale automated and parallel plasmid preparation. Transfection is used to obtain protein expression and often requires microgram to milligram amounts of plasmid DNA. To get these large quantities of plasmid DNA, most researchers perform manual plasmid purifications using spin columns, or columns operated via vacuum or gravity. There are some commercially-available kits for large scale plasmid DNA preparation but compared to the devices and methods described herein, they have a number of drawbacks. Using these kits, it is possible to purify plasmid DNA at the maxi, mega, and giga scales. However, for each scale, the plasmid DNA yield is lower than that obtained from the instant invention. This is because the kits are not able to process as many cells. In these kits, bacterial growth is limited to LB while in the instant invention, it is possible to grow cells using a richer medium such as Terrific Broth. Furthermore, the kit methods are manual and in many cases, cannot be performed in parallel.

Currently, there is only one commercially-available instrument on the market that performs automated plasmid maxipreps, the BenchPro 2100 Plasmid Purification System (ThermoFisher Scientific). However, the BenchPro has significant limitations. The BenchPro instrument is designed to automatically purify two maxi-scale plasmid preparations but it can only accommodate up to 125 mL of bacterial culture grown in LB, a maximum of approximately=$1.25 \times 10^{11}$ total cells. The BenchPro cannot accommodate larger culture volumes or bacterial cultures grown in a rich medium such as Terrific Broth (TB).

The instrument described herein has the numerous advantages over the BenchPro 2100. The BenchPro 2100 is limited to maxiprep scale. In contrast, the instrument of the instant invention is more flexible and can perform plasmid preparations at three different scales: maxiprep, megaprep and gigaprep. There is a limit to the number of cells that may be processed in the BenchPro 2100 instrument. The BenchPro 2100 can only process a total of $1.3 \times 10^{11}$ cells. As a result, the maximum yield of plasmid DNA that can be obtained from the BenchPro 2100 is 1.5 mg. In contrast, the instrument described herein can process up to $3 \times 10^{14}$ cells and plasmid DNA yields can be up to 15 mg.

The BenchPro 2100 instrument can process a maximum bacterial culture volume of only 125 mL grown in LB. In the instant invention, much larger bacterial culture volumes can be processed. Although gigaprep is usually limited to a maximum volume of 3 L bacterial culture, volumes of up to 5 L can be processed in some embodiments. When 5 L of bacterial culture is used, up to $7.5 \times 10^{14}$ cells can be processed. Furthermore, in the instant invention, any medium may be used to grow cells prior to plasmid preparation. This includes media significantly richer than LB such as Terrific Broth, SOB, SOC, YT, 2×YT, Agencourt Ale and other rich media.

The BenchPro 2100 instrument is comprised of several filters that are used at different stages of the plasmid preparation method. The surface area of these filters may limit the capacity of the BenchPro 2100. When too many cells are present, it is possible to plug one or more of the filters, preventing successful recovery of the plasmid. On the other hand, the instrument described herein can operate with only a single large-pore filter. Since the filter has large pores and it is used to perform a filtration step, it is not prone to clogging. Also, the same filter dimensions may be used for the megaprep, maxiprep and gigaprep scale plasmid preparations described herein.

Another limitation found in the BenchPro 2100 is the size of its buffer containers. They are limited to 50 mL. In contrast, the instrument described herein utilizes buffer containers up to 3 L. Larger containers can be used if necessary. In addition, the BenchPro requires a connection to compressed air while the instrument described herein does not.

Therefore, there exists a need for higher yield, larger-scale, automated plasmid preparations. Furthermore, since the BenchPro 2100 is limited to the maxiprep scale, there exists a need for an instrument that can perform megaprep and gigaprep plasmid purifications.

SUMMARY OF THE INVENTION

An automatable method for purifying nucleic acids in a pipette tip column format was developed. Nucleic acids purified by the methods of the invention are substantially endotoxin-free and thereby, suitable for transfection. In some embodiments, nucleic acids are purified after the cell lysis step without the need for cell debris removal. In these embodiments, nucleic acids can be purified directly from an unclarified lysate in an automated fashion.

In other embodiments, cell debris can be partially removed using a partial filtration process. In still other embodiments, cell debris can be completely removed. The method is well suited for purification of plasmids and genomic DNA.

In some embodiments, the plasmid purification process can be scaled up to maxi, mega and gigaprep. In these embodiments, up to 2 L bacterial cultures can be processed using a 20 mL pipette tip column that contains up to 10 mL of resin to obtain up to 15 mg of plasmid DNA.

DETAILED DESCRIPTION OF THE INVENTION

This invention relates to methods and devices for extracting nucleic acids, including plasmids from a sample solution. In U.S. patent application Ser. No. 10/620,155, now U.S. Pat. No. 7,482,169, incorporated by reference herein in its entirety, methods and devices for performing low dead volume column extractions are described. In U.S. patent application Ser. No. 12/767,659, also incorporated by reference herein in its entirety, columns and methods for purification of DNA vectors are described.

It is a goal of the instant invention to develop an automated method for nucleic acid purification and plasmid preparation. In certain embodiments, these methods are performed in a pipette tip column format. In some embodiments, a high-throughput method is desirable. Commonly used commercially-available formats for nucleic acid purification include spin columns, vacuum plates and test tubes.

In the invention described herein, nucleic acids can be purified from any source. In some embodiments, they can be purified from biological sources such as cells. The cells from which nucleic acids are isolated can be eukaryotic or prokaryotic. In certain embodiments, plasmids can be purified from a mixture of nucleic acids or from a gel. Excellent yield and concentration can be obtained using this method. For example, a yield of up to 30 µg of plasmid DNA can be obtained from a 1.4-mL E. coli culture. Plasmid DNA isolated using the methods described herein is substantially endotoxin-free.

Nucleic acids can be purified in an automated fashion. In certain embodiments, plasmids can be purified from multiple samples simultaneously with a robotic workstation or electronic pipette. Typically, automated methods are performed with pipette tips and 96-well plates arranged in a 9 mm center-to-center format. However, other formats are possible, e.g., 4.5 mm center-to-center or 18 mm center-to-center, 36 mm center-to-center, 72 mm center-to-center. In fact, the spacing between pipette tips or pipette tip columns can be in the range of approximately 4.5 mm to 21 cm. In some embodiments, multiple purifications are performed simultaneously in an automated fashion whereas in other embodiments, only one or two samples can be purified. Plasmid DNA can be purified in an automated fashion from up to 3 L of bacterial culture.

It is a goal of the invention is to reduce the number of manual processing steps used for purifying nucleic acids. That is, it is desirable to perform separations with minimal operator intervention.

Figures 5A, 5B:
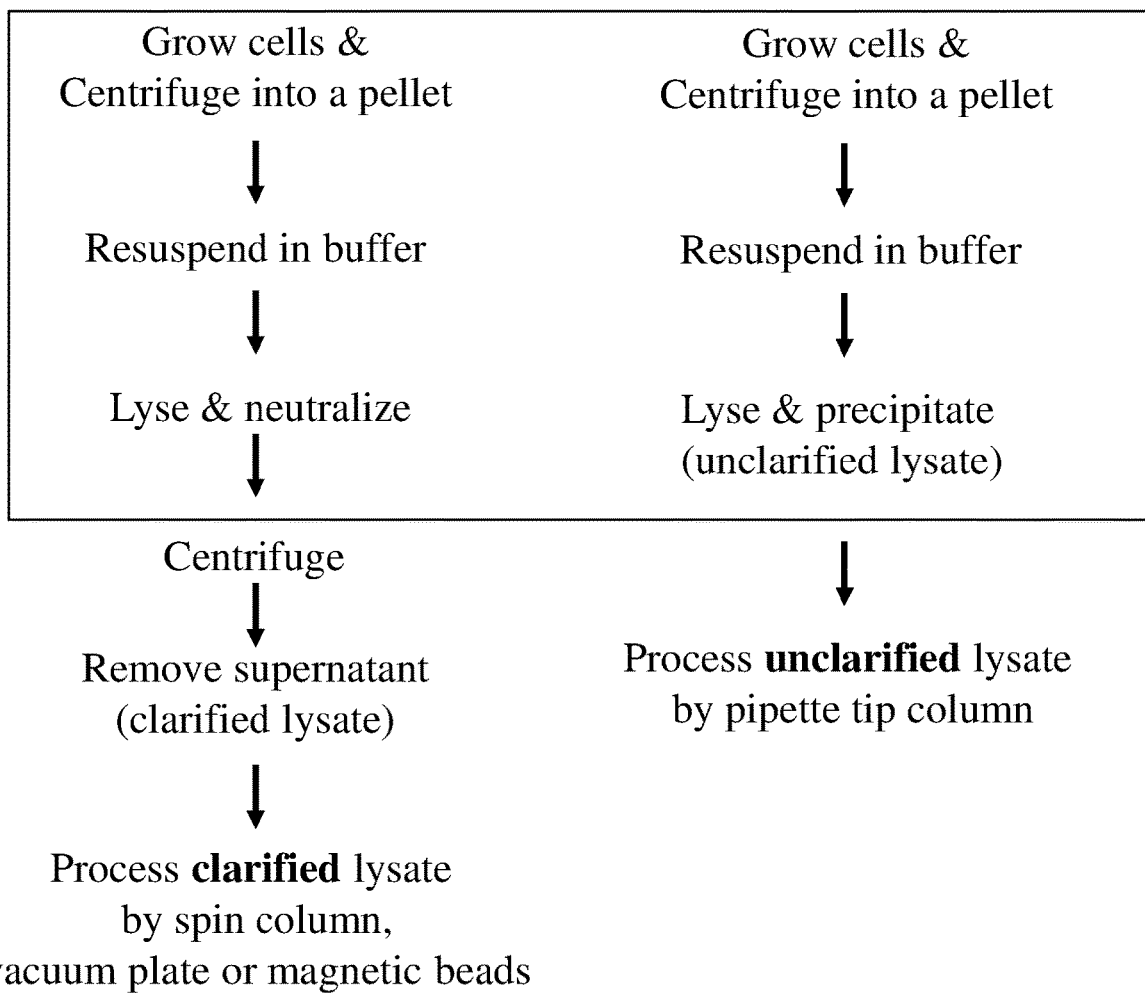
FIGS. 5A-5B is a flowchart comparison of invention versus existing methods.

In certain embodiments, the automated purification procedure begins with resuspension of the cell pellet. That is, nucleic acids are purified directly from an unclarified lysate in an automated fashion (FIG. 5B). There is no need for cell debris removal. Because the method is performed on an unclarified lysate, fewer disposables are needed, purification time is faster and consequently, the cost is lower.

Although it was desirable to eliminate the cell debris removal step and isolate nucleic acids directly from an unclarified lysate, it was technically quite difficult to accomplish. Pipette tip columns provide a unique set of technical challenges not present in other formats such as spin columns or vacuum plates. One challenge is the pump. When using a liquid handling robot, the pressure available to push liquids through the columns is very low compared to centrifugation or vacuum. A second challenge is the volume constraints imposed by the pipette tip column format, particularly with the use of 96-well plates.

In addition, the unclarified lysate is much more heterogeneous, viscous and gelatinous than a clarified lysate. It contains all cellular contents including cell debris, genomic DNA, particulates and liquid. It is surprising that plasmid DNA can be effectively purified from such a heterogeneous mixture.

In other embodiments, the unclarified lysate is subjected to partial filtration prior to nucleic acid isolation. Partial filtration yields a partially-clarified lysate. In still other embodiments, nucleic acids can be purified from a clarified lysate. The clarified lysate can be obtained by centrifugation or filtration.

Before describing the present invention in detail, it is to be understood that this invention is not limited to the specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

Definitions

In describing and claiming the present invention, the following terminology will be used in accordance with the definitions set out below.

Automated methods are defined herein as methods not requiring human interaction.

The term "bed volume" as used herein is defined as the volume of medium or solid phase within a column.

The term "interstitial volume" of the bed refers to the volume of the bed of extraction medium that is accessible to solvent, e.g., aqueous sample solutions, wash solutions and desorption solvents. This includes the space between the beads as well as any volume taken up by the pores within the beads. The interstitial volume of the bed represents the minimum volume of liquid required to saturate the column bed.

The term "dead volume" as used herein with respect to a column is defined as the interstitial volume of the extraction bed, membrane or frits, and passageways in a column.

Endotoxin is defined as lipopolysaccharide or LPS, a cell wall component of all gram-negative bacteria such as *E. coli*. The term, "substantially endotoxin-free" is defined herein as an endotoxin concentration of 100 EU/µg or less.

The term, "flocculent" is defined herein as a precipitate comprised of cell debris and reagents formed after the addition of the lysis buffer and precipitation buffer (if used) to the bacterial cell suspension.

The term "elution volume" as used herein is defined as the volume of desorption or elution liquid into which the analytes or nucleic acids are desorbed and collected. The terms "desorption solvent", "elution liquid", combinations thereof and the like are used interchangeably herein.

The term "frit" as used herein is defined as porous material for holding the medium in the column.

The term "pipette tip column" as used herein is defined as any column containing a solid phase that can engage a pipette, syringe or liquid handler, either directly or indirectly. The term, "pipette tip column" is not limited to columns manufactured in pipette tips. Rather, the column can have any shape or geometry as long as it is capable of engaging a pipette, syringe pump or liquid handling robot. Pipette tip columns can be positioned in a rack or incorporated into a plate.

The term "lysis" or "lysed" is a process by which cells are treated to break the cell wall or membrane and release the nucleic acids.

The term, "plasmid" is defined as an extra-chromosomal, self-replicating nucleic acid molecule. A plasmid can be a single or double stranded and can be comprised of DNA or RNA. Cosmids, fosmids, BACs and YACs are considered to be within the purview of the plasmid definition.

The term, "unclarified lysate" refers to a suspension of lysed cells in which cell debris has not been removed.

The term, "gentle mixing" or "gentle pipette mixing" refers to aspiration/expulsion cycles at a flow rate in the range of 0.1 ml/min-10 ml/min using a wide-bore pipette.

The term, "cycle" as used herein is defined as a single aspirate/expel step.

Purification of DNA from *E. coli*

When purifying plasmid DNA from *E. coli*, the first step is cell growth. A person of skill in the art can select the appropriate medium and growth conditions depending on the cell type, number of samples, desired yield, etc. Culture media can be chosen based on the bacterial strain. A chemically-defined (synthetic) medium is one in which the exact chemical composition is known. A complex (undefined) medium is one in which the exact chemical constitution of the medium is not known. Defined media are usually composed of pure biochemicals off the shelf; complex media usually contain complex materials of biological origin such as peptone, tryptone, blood, milk, yeast extract or beef extract, the exact chemical composition of which is undetermined. Complex media usually provide the full range of growth factors that may be required by an organism so they may be more handily used to cultivate unknown bacteria or bacteria whose nutritional requirement are complex (i.e., organisms that require a lot of growth factors, known or unknown).

Generally, a complex medium is used for cell growth. Complex media include LB, Terrific Broth, SOC, SOB, YT, 2xYT, Agencourt Ale (Beckman Coulter), Plasmid Plus (Thompson Instrument Company) and others. For the purposes of this invention, a rich medium will be defined as belonging to the group consisting of Terrific Broth (TB), SOB, SOC, YT, 2xYT, NZCYM, Agencourt Ale, CIRCLEGROW® (MP BIOMEDICALS), PDM (0.79% Tryptone, 0.44% Yeast extract, 1.0% Glucose, 1.28% Disodium phosphate $7H_2O$, 0.3% Monopotassium phosphate, 0.024% Magnesium sulfate, 0.05% Ammonium chloride), EnPresso and mixtures thereof. For plasmid purification, the growth medium additionally contains the appropriate antibiotic for maintaining the plasmid.

A person of skill in the art can also select the appropriate growth conditions for a given bacterial strain. For a miniprep, bacterial cells can be grown at 37° C. in a 96-well deep-well block with shaking at 300 rpm and harvested in the late logarithmic stage of growth.

Plasmid DNA can be purified from cells grown to a large range of optical densities. It is possible to purify plasmid DNA from cells grown to an $OD_{600}$ of 1, 1, 2, 3, 4, 5, 6, 7, 8, 9 or 10. In some embodiments, plasmid DNA is purified from cells grown to an $OD_{600}$ of less than 1 or greater than 10.

The deep-well block can be selected according to the desired culture volume. For example, a 4-ml deep well block can be used if a larger cell culture is required. Alternatively, cells can be grown in tubes or flasks if a larger volume is required. After the cells are grown, they are centrifuged and the growth medium is decanted and discarded. For convenience, the cell pellets can be frozen at this stage and plasmid DNA can be purified from the cells at a later date or time.

The next step involves resuspension of the cells e.g., in a buffer. In certain embodiments, the remainder of the procedure can be fully automated with the use of a liquid handling system. Generally, mini- and midi-scale purifications can be automated from this step. Maxi-, mega- and gigapreps can be resuspended manually or in an automated fashion.

In those embodiments in which the procedure is automated, a resuspension buffer is added and the cell suspension is repeatedly aspirated and expelled from a pipette tip until the cells are completely resuspended. Alternatively, the resuspension step may be performed manually by shaking or vortexing until the cell pellet is fully resuspended.

After resuspension, the next step is cell lysis. Lysis can be accomplished by a number of means including physical or chemical action. Non-limiting examples of lysis methods include mechanical, such as ultrasonic waves, mortar and pestle, osmotic shock, chemical e.g. by means of detergents and/or chaotropic agents and/or organic solvents (e.g. phenol, chloroform, ether), heat and alkali. Lysis via chemical means can be performed on a liquid handling system by addition of a lysis solution to the resuspended cells.

When purifying plasmid DNA, a precipitation buffer can be added to the lysed cell suspension to precipitate the genomic DNA prior to plasmid capture. In certain embodiments, the precipitation buffer is comprised of chaotropic salts. Gentle mixing with a wide-bore pipette tip and a relatively low flow rate can be used at this step. After lysis, the plasmid is captured using a pipette tip column.

In existing commercially-available methods, a centrifugation step is usually performed following cell lysis to pellet cell debris. However, an advantage of the instant invention is that this centrifugation step can be bypassed making the method considerably more automated than other methods. In alternate embodiments, the sample can be centrifuged or filtered to produce a clarified lysate. In certain embodiments, the sample is partially filtered to produce a partially clarified lysate.

To prepare the column for use, it can be equilibrated with water or buffer prior to the capture step. Equilibration can be performed by a single aspiration and expulsion of water or buffer from the column. Alternatively, an equilibration solution can be passed through the column in a top-down fashion.

After the pipette tip columns are equilibrated, DNA can be captured on the equilibrated column by repeated aspiration and expulsion. In alternate embodiments, the sample is captured using gravity flow. In still other embodiments, nucleic acids are captured using vacuum.

After capture, the columns are usually washed to remove non-specifically bound materials. One or more wash steps can be performed. When more than one wash is performed, the same wash solution can be used for multiple washes or different wash solutions can be used. In certain embodiments, the wash solution contains an organic solvent, e.g., alcohol.

Wash steps can be performed with back and forth flow, or unidirectional flow using gravity or vacuum. One advantage of performing the wash steps by unidirectional flow is that higher throughput can be achieved. That is, when nucleic acid purification is performed on a liquid handling robot, throughput can be increased by utilizing the liquid handling head simply for dispensing wash solution to multiple plates. When the wash is performed by back-and-forth flow, the liquid handling head can process only one plate (96 samples) at a time.

After the wash step, air is passed through the columns to remove any organic solvent remaining from the wash step. This can be accomplished by depositing the pipette tip columns onto a drying station or vacuum block and drawing air through the columns with a vacuum. A vacuum block adaptor or drying station was custom built for this process and is integrated into the instrument deck. The drying station is described in more detail below.

In certain embodiments, air is passed through the columns long enough to remove the organic solvent present in the wash solution, but not long enough to dry the columns completely. In other embodiments, the columns can be dried completely. When the residual organic solvent is measured, it is in the range of less than 10%, less than 9%, less than 8%, less than 7%, less than 6%, less than 5%, less than 4%, less than 3%, less than 2% or less than 1%.

In other embodiments, air is passed through the columns with positive pressure. Alternatively, it is possible to dry or remove the ethanol or other organic solvent after elution by methods such as speed-vac, air drying, heating or applying a gas stream to the wells containing the eluted sample.

The elution of DNA from the columns can be accomplished with back and forth flow or unidirectional flow. Generally elution volumes are in the range of about 1-5 times the bed volume. When back-and-forth flow is used, air can be aspirated into the pipette tip column prior to aspirating the elution buffer. This air can be used after expulsion of the DNA to ensure complete expulsion of all the liquid in the column.

Generally, the elution buffer is aqueous and has a pH between 6 and 10. In some embodiments, the column is incubated with the elution buffer for a period of time. In these embodiments, the column and elution buffer are incubated for at least 1 minute, at least 2 minutes, at least 3 minutes, at least 4 minutes, at least 5 minutes, at least 10 minutes or at least 15 minutes. In other embodiments, the incubation step is omitted.

After the incubation step, the purified DNA is expelled from the pipette tip column. To ensure the maximum volume of purified DNA is recovered, a blow-out step can be performed by expelling the air aspirated as described above.

When plasmid DNA is purified by the methods of the invention, generally the concentration is at least 25 ng/µL. In some embodiments, the concentration of purified plasmid DNA is at least 50 ng/uL, at least 75 ng/uL, at least 100 ng/uL or greater. The $A_{260/280}$ ratio of plasmid DNA purified by the methods of the invention is in the range of 1.8 to 2.0. Most importantly, the plasmid DNA purified by these methods is high quality, substantially free of endotoxin and can be used for any downstream application including sequencing, transfection and transformation.

The entire process from cell harvest to eluted plasmid DNA generally takes between 30 minutes and 1.5 hours. However in some embodiments, the entire procedure can be performed in the range of 40 to 80 minutes or between 45 and 75 minutes.

Plasmid Preparation Method Development

To develop a robust method for purifying plasmid DNA from an unclarified lysate, experiments were performed in which plasmids were purified from E. coli cells. After the cells were grown, they are collected by centrifugation and the growth medium is discarded. step for purifying nucleic acids is cell lysis. Lysis can be carried out by a number of means including the use of chemicals i.e., detergents or by mechanical/physical means, such as temperature or sonication.

Currently, the predominant commercially-available formats for plasmid purification are spin columns, magnetic beads and vacuum plates. In these methods, cell debris is usually removed completely by centrifugation after the lysis and neutralization steps to obtain a "clarified lysate" from which nucleic acids are purified (FIG. 5A). The clarified lysate is free of all cell debris and flocculent. Complete removal of cell debris to produce a clarified lysate is most often accomplished by centrifugation but some vacuum plate methods utilize filtration. These methods are undesirable because they are time-consuming and difficult to fully automate, making it quite laborious to purify nucleic acids from multiple samples simultaneously. Furthermore, when filtration is used, the filter is prone to clogging. Partial filtration is not subject to the same pitfalls.

Formats for plasmid preparation via vacuum include individual columns and multi-well plates. Even after producing a clarified lysate, these methods are not well suited for automation. Some protocols recommend turning off the vacuum while adding reagents, which requires operator involvement. Additionally, differences between samples can cause differential column pressures between columns or wells within the plate so an operator is often needed to ensure the vacuum manifold seal is maintained or that the liquid sample flow occurs evenly through all the wells of the plate. Since spin columns require a series of centrifugation steps, they are not amenable to automation without special equipment. Magnetic beads are expensive and require repeated shake and aspiration steps, which makes their use difficult to automate. Magnetic beads or other bead suspension methods that do not first remove the cell debris are not reproducible and are difficult to automate.

An advantage of the instant invention is that plasmids can be purified in parallel, up to 96 samples at a time without operator involvement. With proper instrumentation, multiple plates of 96 samples can be processed simultaneously.

An experiment was performed to compare the viscosity of the unclarified lysate to that of a clarified lysate. An overnight culture of *E. coli* harboring a plasmid was subjected to centrifugation, resuspension, lysis and precipitation. A clarified lysate was made from half the mixture and the viscosity was compared to the corresponding unclarified lysate. For each sample, the efflux time was measured using a size 400 Cannon-Fenske Routine Viscometer. The efflux time is the time it takes for the solution to travel between two points within a glass tube. The efflux time for the unclarified lysate was almost twice as long as that for the clarified lysate (2.17 seconds vs. 1.18 seconds). The kinematic viscosity was calculated to be 2.6 centistokes for the unclarified lysate compared to 1.4 centistokes for the clarified lysate. In the some samples including the more concentrated midiprep (described below), the viscosity of the unclarified lysate can be even higher. In certain embodiments, the viscosity can be in the range of 2 centistokes to 7 centistokes, or in the range of 2.5 to 5 centistokes.

In U.S. patent application Ser. No. 12/767,659, a first approach to plasmid preparation from an unclarified lysate was described. Although the invention described in U.S. patent application Ser. No. 12/767,659 was an advance over other methods, the results obtained were still inconsistent. Sometimes, the columns plugged with particulates contained in the unclarified lysate. In some cultures, the particulates seemed to be greater in mass and all or most of the columns plugged. Even if the procedure worked without incident at times, the recovered, purified vector performed well for sequencing but sometimes couldn't be used effectively for transfection or transformation. Another problem observed was that the $A_{260}$ was artificially high at times, particularly when the plasmid was present in a low or medium copy number. After plasmid purification, the concentration was measured by UV and also by a semi-quantitative measurement of the intensity of the plasmid band on an agarose gel. The comparison of these two methods suggested that something present in the sample might be co-purified with the plasmid, causing the $A_{260}$ to be artificially high.

In the instant application, these problems were solved making the method significantly more robust and reliable. Better sampling and purification methods were developed along with methods that allow scale-up in an automated format. The quality and purity of the product was improved making it useable for a greater variety of downstream applications.

To address the problem of random column plugging and increase the reproducibility of the method, we examined and developed an entirely new sampling procedure. It was discovered that the amount and type of particulate in unclarified lysate varied depending on a number of parameters including medium, strain, replicon, growth time and conditions. It turned out that the distribution of the cell debris present in the sample differed dramatically between samples. Sometimes the debris was distributed more or less throughout the sample, sometimes the majority of the debris floated, but in other instances a portion of the cell debris sank. This variability seemed to be one reason the method was not reproducible and that sometimes the columns plugged. Another reason seemed to be the amount of mass particulate varied tremendously from sample to sample. In some cases, the floating mass of particulate appeared to take up a large part, or even most of the sample.

It was desirable to use all the liquid in the unclarified lysate in order to obtain the maximum amount of plasmid DNA. However, particulate masses present in the lysate contained liquid that appeared entrained and occluded. There did not appear to be active exchange of the occluded liquid with the other liquid in the sample.

Generally, in a suspension of particulates and liquid, the liquid can move freely throughout the sample. But when masses or globs of particulate accumulate in a sample in a stable form, free movement of the liquid within the mass is halted. The mass of particulate is almost like a large hydrated bead; there is no active transport of liquids but only diffusion. The masses within the unclarified lysate looked globular and gel-like. It was speculated that plasmid contained in these globules would be unreachable unless the masses were broken up because active transport of liquid in and out of the mass would be limited. In the methods described in U.S. patent application Ser. No. 12/767,659, the entire sample was passed through the pipette tip column. Passing these masses through the column broke up the masses and allowed capture of the plasmids. The only way to capture plasmid contained in the entire sample, including the sample within this occluded liquid, was to pass the entire sample through the column. This method worked because the pipette tip columns are designed to allow particulates to pass through however, the columns clogged at times. It was desirable to develop a method that reduced the amount of particulate in the sample while still allowing automation.

Improved Sampling Method

A novel sampling method was developed to improve plasmid isolation from the unclarified lysate. First, the solutions were changed. In patent application Ser. No. 12/767,659, we used a lysis solution followed by a neutralization buffer comprised of a chaotropic salt, a salt and an acid. However, it was determined that it was more effective to use two solutions sequentially. The lysis solution was first followed by a solution for neutralization (acid and salt) and then a second solution containing the chaotropic reagent. When a solution containing salt and acid were added prior to the chaotropic salt solution, the $A_{260}$ more accurately matched the plasmid concentration obtained by the agarose gel band intensity. In addition, the amount of precipitate or cell debris generated seemed to be more uniform.

However, this did not solve the reproducibility and plugging issue. There were still large amounts of particulate masses in the sample that contained entrained liquid. In some cases, these masses floated, while in other cases, the masses precipitated. Some particulate remained in suspension of the sample but depending on the cell growth conditions and time, the mass of cell debris appeared to make up about 20-50% (vol/vol) of the sample.

In most commercially-available methods, the sample is centrifuged at this stage and the supernatant (the clarified lysate) is used from plasmid capture. Once the sample has been centrifuged, the liquid is very easy to process using spin columns or plates.

In the unclarified lysate used in the invention, it is likely that the actual solids content in the masses was only a very small portion of the sample. But having a substantial proportion of the sample entrained or occluded within the floating or sinking masses seemed to be the major issue. The liquid entrained within the mass of solid did not appear to be available for capture unless there was active transport of the liquid to the resin in the column.

A second change made to the sampling procedure was that only a portion of the sample was aspirated and expelled. Instead of aspirating the entire unclarified lysate, only a portion was sampled. Quite unexpectedly, it was determined that as little as 10% of the total volume could be repeatedly aspirated and expelled and the yield was not affected provided the number of cycles of liquid traveling through the column was increased. The term, "cycle" as used herein is defined as a single aspirate/expel step.

Without being bound by theory, it is possible that the mass of particulate broke up and reformed with each expulsion of the liquid back into the sample thus releasing or exchanging some of the entrained liquid. It did not seem possible that diffusion of the plasmid from the occluded liquid could occur because the distance to diffuse would be several millimeters and could even be more than a centimeter in some cases.

The experiments showed that sample volumes as low as 10% of the total volume in the well could be sampled and still get adequate recovery. As much as 90% of the volume could be sampled while still eliminating plugging of the column and get good recovery of the plasmid DNA. Preferably, between 10 and 90% of the sample volume can be sampled, more preferably 20-80% of the volume can be sampled, more preferably 30-70% of the volume can be sampled, more preferably 40-60% of the volume can be sampled, most preferably 35-50% of the unclarified lysate volume can be sampled. These results were unexpected and surprising in light of the fact that the particulates were often globular and appeared to have liquid sample entrained which had appeared to prevent capture of the plasmid within this liquid volume.

In some embodiments, the sampling procedure was modified to include the addition of an aspirate and expel step prior to plasmid capture. This step was performed while the pipette tip columns are attached to the robotic head. Air was drawn into the columns slowly and then the columns were submerged in the sample and the air was slowly expelled through the columns into the unclarified lysate. The additional aspiration step caused the bulk of the particulates to float which more effectively kept them farther away from the open lower end of the column during the subsequent aspirate/expel cycles used for plasmid capture.

In certain embodiments, a carbonate, e.g. ammonium carbonate can be added to the sample to make the flocculent float. In fact, any carbonate compound can be used.

Improved Plasmid Quality

In U.S. patent application Ser. No. 12/767,659, removal of the interstitial liquid from columns by vacuum or air pressure was described. Only a short duration of vacuum or air pressure is required to remove this bulk (interstitial) liquid: 0.1-1 minute or even between 5 and 30 seconds depending on the force of the vacuum or air pressure.

In the methods described in U.S. patent application Ser. No. 12/767,659, bulk liquid was removed and the plasmid or nucleic acid was recovered from the column by passing water or buffer through the column. The quality of the plasmid was good and it was suitable for downstream processing such as sequencing, mutation analysis, etc. However, it was discovered that the plasmid recovered from this process could not be used successfully for transfection. Gels of the purified plasmid showed pure, concentrated plasmid yet, transfection frequency was very low.

The procedure described in U.S. patent application Ser. No. 12/767,659 yielded a suitable quantity of plasmid DNA that performed well in DNA sequencing, however it was discovered that the baculovirus transfection and bacterial transformation efficiency were both unexpectedly low. Initially, it was thought that the low transfection frequency was due to contamination with protein, guanidinium or perhaps endotoxin. Endotoxin was measured as described below and protein was measured by absorbance at 280 nm. As a result, endotoxin and protein were ruled out as contaminants. It was considered that there could be a nucleic acid contaminant in the recovered plasmid such as genomic DNA or RNA. However, it wasn't possible to directly measure the genomic DNA or RNA contamination.

Finally, it was suggested that a measurement should be performed of residual solvent in the recovered plasmid since the Wash buffer contained ethanol. The columns appeared to be free of solvent before the elution step and there was no indication that the recovered plasmid contained any ethanol. The interstitial liquid in the column prior to elution appeared by visual inspection to be completely removed.

A Carl Zeiss single optic hand-held refractometer was used to measure the alcohol content in the purified plasmid. Aqueous standards containing known concentrations of ethanol were prepared and an analysis of the recovered plasmid was performed on several samples. Surprisingly, the samples of purified plasmid contained considerable amounts of ethanol, in the range of 5-15% (vol/vol). This result was surprising because it was thought that ethanol would prevent efficient elution of the plasmid from the column. There is no alcohol in the elution solvent in order to get efficient elution. The presence of ethanol was also surprising because a miniprep performed using a commercially-available spin column method produced a final alcohol content in the recovered plasmid in the 2-3% range. So clearly, something about the columns or the method caused the residual ethanol to be present.

It was known that as the particle size of the resin used in the pipette tip columns was large. This was because the frit pore size of the columns had been increased to reduce plugging and therefore the particle size of the resin was also increased so that it did not fall out of the column. Without wishing to be bound by theory, it was known that the resin can contain pores to increase surface area and facilitate plasmid capture. Unfortunately, the resin appeared to retain much more solvent than the spin columns, possibly due to its higher porosity and greater surface area. In addition, the centrifugal force applied to spin columns is probably quite efficient at vacating any liquid remaining in the column. This retained solvent may have contributed to the higher percentage of ethanol present in the eluted plasmid. Alternatively, the higher percentage of alcohol obtained from the pipette tip columns and method could have been due to some other unknown phenomena.

Several different remedies were tested to solve the problem of residual organic solvent in the purified plasmid. The first method evaluated was simply to lift the columns out of the wash solution and pass air back and forth through the column with the robotic pipette head. Even though the resin bed appeared to be equally wet at the beginning and end of the process, the amount of organic solvent in eluted plasmid decreased. While this method would likely work if the back and forth flow was performed with adequate number of cycles, it was not preferred because it added too much additional time to the method.

Other options to pass air through the columns were considered. Air could be forced through the columns by positive pressure however, this would require an additional apparatus be designed and built. Vacuum could be used, not only to remove bulk liquid, but as an additional step implemented to move air through the columns after the bulk liquid had been removed from the interstitial space. A vacuum pump rated to pull 4 cubic feet per minute through the pump at zero vacuum was used to pull air through columns under a number of different conditions.

These first experiments involved forcing air through set of 80 μL bed columns in a 96 well format and measuring the effect of total air through the system. After 1 minute and removal of the interstitial liquid, the total air pulled was measured to be 4 cubic feet. The measurement was performed by taking a venturi-type air flow meter and connecting the meter to the vacuum in the reverse connection so that the air pulled through the meter was measured (rather than the normal measurement of air pushed through the meter). The initial experiments showed that the liquid was pulled through the column. After the initial liquid was removed, air appeared to be pulled through the columns.

The vacuum method was investigated by depositing the pipette tip columns into a vacuum station on the robot deck and passing air through the columns using vacuum. An oil vacuum pump (0.5 horsepower) was used to pull a vacuum of 4 ft$^3$/min through the columns. This use of vacuum is quite distinct from the traditional use of vacuum. Traditionally, vacuum is used to pull liquid solutions through plates or columns. After the solution passes through the plate or column, the vacuum is turned off because the task has been accomplished. In the case of the instant invention, the wash solution had already been passed through the columns and the vacuum is used simple to draw air through the columns.

However, when measurements were performed with an air flow bubble meter (also connected in reverse) on individual wells, it was determined that the air flow after the interstitial liquid was removed from the column was not consistent from column to column. In fact, it was found that no air, or very little air was flowing through many of the columns while other columns had significant air flow-through. Upon further investigation, it was determined that once the initial liquid had been removed from the columns, the vacuum seal formed for each column was inconsistent. Analysis by refractive index of the elution solvent pulled through a number of columns indicated there was a correlation between the quality of the vacuum seal and the amount of ethanol recovered with the solvent. That is, those columns with a poor seal contained more ethanol while those columns having a good seal contained less. However, there was no difference in appearance of the individual columns. They all looked as though the interstitial liquid had been removed and they all looked equally wet with surface liquid.

The next process tried was use of a 96-well aluminum heating block oven and a forced air oven. The ovens were set to 37-42° C. After final wash and expulsion of as much liquid as possible, the columns were placed in the ovens for 10-30 minutes. Again, the columns appeared wet after incubation in the ovens however, the ethanol concentration was reduced to as low as 5%. This result was encouraging however, the time required was still longer than desired.

It was necessary to build a custom 96-well vacuum block. To test the effectiveness of the vacuum block, it was necessary to build two additional air flow measurement apparatus. It was not possible to measure the air flow by seeing the liquid flow through the columns. The air flow had to be measured directly. The first apparatus was a cover for the vacuum block that was attached to and air gauge and used to measure air flow through the entire block. The air gauge (King Instrument Company, Part No. 75201102C17) was actually used in reverse. That is, air was pulled through the top of the gauge rather than being pushed through the bottom of the gauge as it was designed. Using this cover, a reading greater than 0.4 cfm was achieved with the pump and block being tested. Lifting the block from the vacuum manifold showed that there was a good seal between the vacuum block and its manifold base.

After redesigning of the vacuum block, the air pulled through by vacuum after the interstitial liquid was removed became more consistent between columns. More ethanol was found when the air flow was slower, even though the columns appeared the same regardless of the airflow duration. It turned out, the vacuum generally pulled air through the column on an equal basis although the columns on the outside of the vacuum block still had higher flow than the center columns. Presumably this simple design permitted vacuum to pull the interstitial liquid through the columns, but once this was done, the vacuum applied to the columns was insufficient to apply uniform vacuum to all of the individual columns.

Several vacuum blocks were built before an adequate block design was found. The first block built had 96 positions on the top for the columns and an open architecture on the bottom of the block. The air flow through the block seemed adequate. However, it was not possible to get a tight seal when this block was tested with the cover. It seemed possible that while the total air flow may have been adequate, the air flow across the individual columns could differ dramatically.

A second custom apparatus was built to test the vacuum through individual columns seated in the vacuum block. In this case a bubble meter tube for measuring gas flow out of a packed bed gas chromatograph was modified to measure vacuum. A Wilmad LabGlass 10 mL gas flow bubble meter was adapted to measure air flow through the individual columns. As with the other gauge, the vacuum was applied to the top of the meter tube, leaving the tube fitting open that would normally have been the inlet from the gas chromatographic column. 96 columns were placed in the block and the air flow through each column was measured. Using this gauge, it was discovered that flow was not even between the columns. To solve this problem, the vacuum block was redesigned to have a gasket seal around each column.

The design of the column seal(s) proved to be difficult. The seal had to be tight enough to seal all of the columns routinely and adequately. But the column had to be easily placed into the apparatus and it must be possible to remove the columns from the block without the block being pulled up along with the columns. The seal cannot be so tight as to prevent engagement of the columns by the robotic head. If the columns seals were too tight, attempting to remove the columns from the block could result in the block being lifted with the columns. So the seal could not be too tight. After several redesigns the block applied vacuum evenly through all the columns. Interestingly, it was not possible to determine whether air flowed through a particular column or not by visual inspection. Only the custom measurement tools could provide this information.

The redesign of the vacuum block provided a tighter seal around each column while still allowing the columns to be removed from the block. After the redesign, experiments were performed to determine how much airflow was needed to remove the residual ethanol from the column. The level of vacuum and the vacuum duration were varied. In another set of experiments, the number of columns to which vacuum was applied was varied while keeping the vacuum level constant. In all experiments, the column appeared dry by visual inspection before and after the vacuum was applied. The results showed that for 96 columns with an 80 μL bed volume, a vacuum of 4 cubic feet per minute (CFM) applied for between 1 to 20 minutes (above and beyond the vacuum needed for removal of the interstitial liquid) was needed to lower the ethanol concentration of the eluent to 0-5%. This corresponds to an amount of 4-80 cubic feet of air passed through 96 columns.

The next step involved testing the vacuum procedure for removal of the organic solvent present in the wash solution. Liquid containing various amounts of ethanol was cycled through the columns. The columns were placed in the vacuum block and vacuum was applied for varying amounts of time. The columns were eluted with water, the eluent collected and the refractive index was measured for organic solvent concentration. After the solvent removal step, the columns still appeared wet by visual inspection. To maintain the highest possible throughput, it was desirable to find the shortest possible vacuum duration that resulted in purified plasmid having acceptably low alcohol content. Although the solvent drying step is an additional step to the process, if a very strong vacuum is used, the columns can be dried more quickly without sacrificing throughput.

Depending on the vacuum applied and the air flow through the individual columns, the "drying time" can be between 30 seconds and 20 minutes, but preferably between 2 and 5 minutes. Drying time is defined as the time that vacuum or air flow is applied after the removal of the bulk liquid (which can also be done by vacuum or air). Based on these experiments, a vacuum duration was determined for which the eluent contained an acceptable amount of ethanol. Preferably, the percentage of ethanol in the purified plasmid is less than 10%, less than 9%, less than 8%, less than 7%, less than 6%, less than 5%, less than 4%, less than 3%, less than 2% or less than 1%. Less than 5% solvent was preferred and less than 3% was most preferred.

In other embodiments with longer drying conditions, it is possible to dry the columns completely prior to elution of the purified plasmid. However, good results were obtained when the solvent was substantially removed and the columns were not dried completely after the final wash and prior to elution.

Implementation of the solvent removal step affected the reproducibility of the elution step. For example, when 80 μL bed silica columns were subjected to vacuum to remove the organic solvent present in the wash, 130 μL of water was used for the elution step and only 80-90 μL of liquid was collected. This result indicated that a significant portion of the water was trapped in the dead volume of the pipette tip column.

To help mitigate this problem, the elution step can be modified. An additional step can be added at the end of the procedure to maximize the elution volume. Air can be taken up by the robotic pipetting head after the solvent removal step and prior to engagement of the columns for elution. This added air is then expelled after expulsion of the purified plasmid to get as much liquid as possible out of the column.

Yield can also be increased by incubating the elution solution on the column prior to expulsion. As an example, the elution solvent can be aspirated and incubated on the column for 5 minutes prior to expulsion.

Partial Filtration

After lysis and optional addition of the precipitation buffer, the sample contains a flocculent comprised of reagents and cell debris. It can be advantageous to remove some of the flocculent by partial filtration. Although the columns can tolerate particulates in the sample, the sample can be processed more rapidly and more completely if cell debris is at least partially removed. After the partial filtration step, the lysate still contains some particulates. Since the filtrate still contains some cell debris, it is not considered a clarified lysate. Instead, the filtrate is called "a partially-clarified lysate."

A filter with very large pores can be used to remove some of the flocculent. A large-pore filter is defined herein as a filter having a pore size larger than 25 μm. In certain embodiments, the large-pore filter has a pore size greater than 30 μm, 35 μm, 40 μm, 45 μm or 50 μm. Generally, the pore size for a large pore filter is in the range of 50 micron-3000 micron. For partial filtration, a large-pore filter is used. The pore size of the filter is generally in the range of 200 to 2000 μm. In certain embodiments, the pore size is in the range of 500 to 1500 μm, 600 μm to 1000 μm or 700 μm to 900 μm.

Partial filtration performed with a large-pore filter quite unorthodox. While commercially-available filters generally have a pore size of 25 micron or less, the pores of the large-pore filter are much larger. In the large-pore filter, the pores are larger than some of the particulate material found in the sample. As a consequence, some particulate material goes through the filter. In contrast to conventional filters, the large-pore filter is not designed to filter all particulate; just a majority of the particulate material.

In addition, the large-pore filter is designed to operate under gravity, pressure, low pressure or vacuum, even in automated embodiments. In some embodiments, the large-pore filter can operate at low pressures. For example, the filter can operate at less than 20 psi, less than 15 psi, less than 10 psi, less than 5 psi, less than 4 psi, less than 3 psi, less than 2 psi, or less than 1 psi.

In other embodiments, the pore size of the filter can be 10 μm or more. In these embodiments, the filter pore size can be greater than 10 μm, greater than 15 μm or greater than 20 μm.

For automated embodiments, it is unusual to have a filtration apparatus operated using gravity because the filtration rate is unknown. The amount of particulate is sample-dependent and therefore unpredictable. Generally, automated procedures require pre-programmed times and volumes. Similarly, it is unusual to have in automated filtration process operated using low pressure or vacuum.

After the lysis and precipitation steps, the sample can be contained in a tube, centrifuge bottle or another type of container. In certain embodiments, the sample can be transferred to the partial filtration apparatus in an automated fashion. In other embodiments, the container, tube or centrifuge bottle harboring the precipitated sample can be placed above the partial filtration apparatus and pierced in such a way that the sample flows into the filter.

Alternatively, the precipitated sample can be poured into the partial filtration manually and the automated procedure can begin during the partial filtration step. While the precipitated sample is undergoing partial filtration, aliquots of the filtrate can be removed from the filter apparatus and passed through the column to capture plasmid DNA. In some embodiments, automation begins early in the plasmid purification process, e.g. at the cell pellet resuspension step. In other embodiments, the automated process can begin during or after partial filtration, particularly for larger preps such as maxiprep, megaprep and gigaprep.

Partial filtration using gravity flow can be performed in 60 minutes or less, depending on the scale. In some embodiments, gravity-flow partial filtration can be performed in 50 minutes or less, 40 minutes or less, 30 minutes or less, 20 minutes or less, 10 minutes or less, 5 minutes or less, 2 minutes or less, 90 seconds or less, 1 minute or less or 30 seconds or less. A maxiprep scale, gravity-flow partial filtration can take between 10 seconds and 3 minutes. For a megaprep or gigaprep, the partial filtration step can take between 30 seconds and 9 minutes.

In some embodiments, the filtrate can be collected and filtered through the same filter apparatus a second time. For re-addition of the filtrate to the filter, as you increase the volume added, the time also increases. Time ranges based on scale and volume are listed below.

Maxi (100 mL re-addition): 1-10 minutes
Maxi (200 mL re-addition): 10-30 minutes
Mega/Giga (100 mL re-addition): 3-20 minutes
Mega/Giga (200 mL re-addition): 20-60 minutes In certain embodiments, two filters can be used in the filter apparatus in parallel.

The filter can be comprised of any material or combination of materials. Nonlimiting examples include plastic, metal, nylon, glass, paper and cloth as well as any of the materials listed below in the section on frits. In some embodiments, the filter is a coarse or porous cloth. In these embodiments, several layers of cloth can be used. Smaller particles pass easily through the cloth filter, but much of the particulate is retained.

The filter pores can have any geometric or irregular shape. For example, the pores can be round, oval, square, rectangular or polygonal. For pores that are not round, pore size is defined herein as the average of the longest distance across the pores.

Partial filtration generally removes between 50% and 99% of the flocculent or cell debris. Conversely, 1% to 50% of the flocculent/cell debris can pass through the large-pore filter. Since the density of the flocculent/cell debris is similar to that of water, 50% of the flocculent/cell debris can be considered either 50% (wt/vol) or 50% (vol/vol).

In certain embodiments, partial filtration can remove between 60% and 99%, between 60% and 98%, between 65% and 97%, between 70% and 96% or between 80% and 95% of the flocculent. In other embodiments, partial filtration can remove between 50% and 97%, between 50% and 96%, between 50% and 95%, between 60% and 90% or between 70% and 90% of the flocculent. In terms of the percentage of flocculent that can pass through the filter, that can be between 1% and 40%, between 2% and 40%, between 3% and 35%, between 4% and 30%, or between 5% and 20%. The percentage of the flocculent that passes through the filter can be calculated by determining the volume of the flocculent and the total volume of the filtrate.

In other embodiments, more than 99% or more than 99.5% of the flocculent is removed by partial filtration or filtration. In these embodiments, between 99% and 100% of the flocculent is removed.

In some embodiments, the filter is vertical while in other embodiments, the filter is horizontal or at an angle between vertical and horizontal. The area of the filter may be at least of 3 $cm^2$, 5 $cm^2$, 10 $cm^2$, 20 $cm^2$, 30 $cm^2$, 40 $cm^2$, 50 $cm^2$, 60 $cm^2$, 80 $cm^2$, 100 $cm^2$, 125 $cm^2$, 150 $cm^2$, 200 $cm^2$, 400 $cm^2$, 600 $cm^2$, 800 $cm^2$ or at least 1000 $cm^2$.

In some embodiments, a single filter is used to remove particulate from the plasmid sample. In some embodiments, two or more filters operated in series may be used to remove particulate from the plasmid sample. When two or more filters are used in series, it is possible to remove most or all of the particulate from the sample. In other embodiments, the filtrate may be collected and put through the filter a second time.

Figure 6:
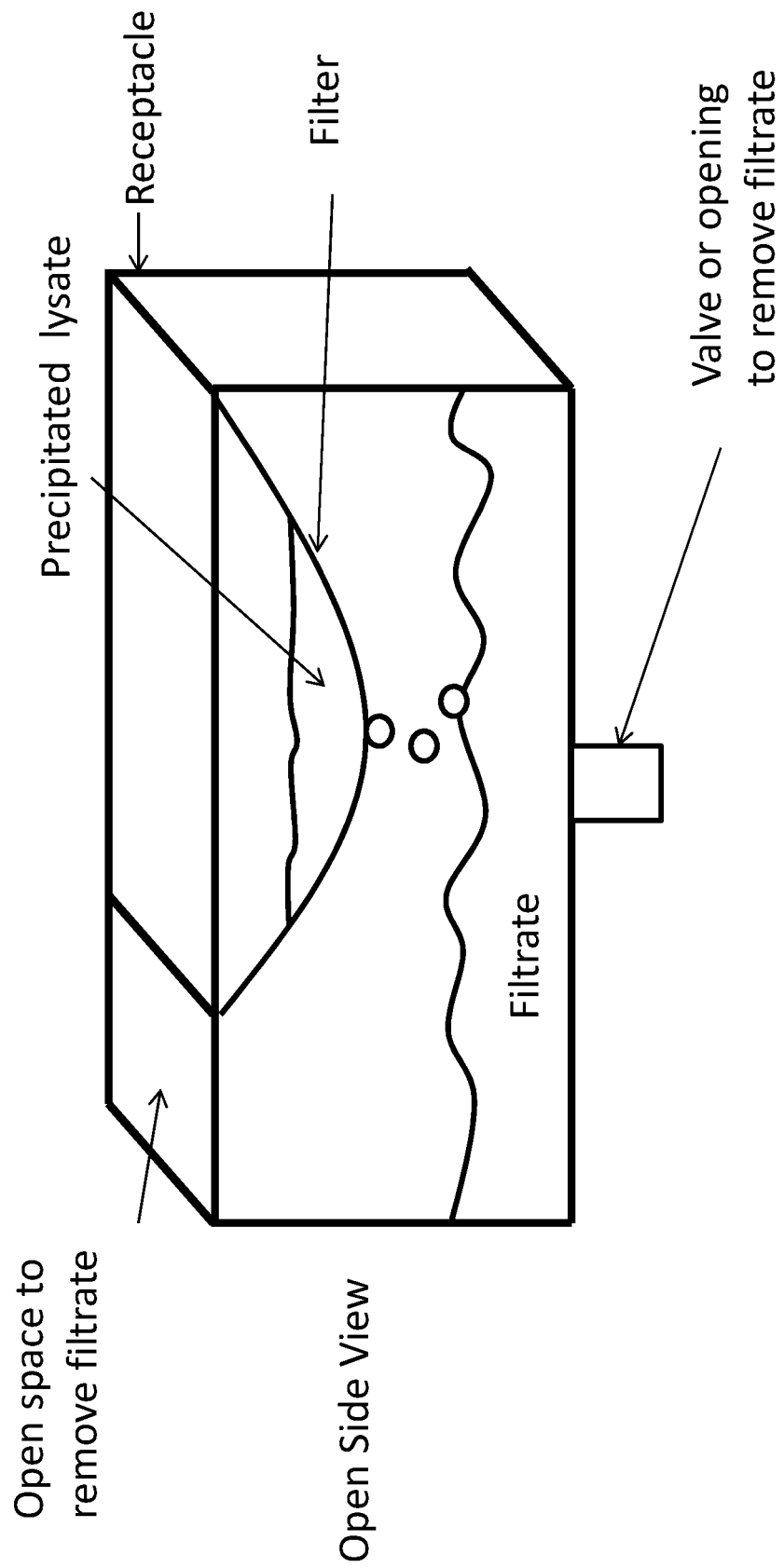
FIG. 6 depicts a cut-away view of one embodiment of the partial filtration apparatus.

FIG. 6 shows a cut-away view of one embodiment of a partial filtration apparatus. The precipitated lysate is deposited on a filter. The filter is positioned within a receptacle. In certain embodiments, the filter is a large-pore filter. The filtrate can be a partially clarified or in certain embodiments, the filtrate can be a clarified lysate. Following the filtration process, the filtrate can be removed through the open space adjacent to the filter or through the valve or opening below the receptacle.

Endotoxin Removal

Endotoxin is an abundant lipopolysaccharide present in the cell wall of gram-negative bacteria such as *E. coli*. It is undesirable to have endotoxin molecules in the purified plasmid DNA because it can stimulate the mammalian immune system, decreasing transfection efficiency.

Several different methods can be used to remove endotoxins from nucleic acid samples. For purification procedures that use ethanol precipitation, endotoxin is commonly removed during the ethanol precipitation step. For procedures that don't employ ethanol precipitation, a dedicated resin can be used for endotoxin removal (see U.S. Pat. Nos. 6,194,562 and 6,942,802). Another method involves a borate wash (see U.S. Pat. No. 7,935,505). Yet another technique for endotoxin removal involves enzymatic destruction as described in WO2007115046.

In the instant invention, none of the methods described above are used. Nucleic acids are captured on the column, the column is washed and the nucleic acids are eluted. The wash solution does not contain borate.

An endotoxin test was carried out to examine concentration of endotoxin obtained from miniprep spin columns versus the miniprep pipette tip columns and methods of the invention. Plasmid DNA was purified in triplicate from *E. coli* pellets as described above. Additionally, plasmid DNA was purified in duplicate using a spin column method (Qiagen Cat. #27104) according to the manufacturer's protocol. The plasmid DNAs were tested using a ToxinSensor Chromogenic LAL Endotoxin Assay Kit from Genscript (Cat. L00350C). Using the supplied endotoxin controls, a standard curve was generated, and the amount of endotoxin in the plasmid DNA preparation was quantified. In all cases, endotoxin was measured to be less than 0.01 endotoxin units per microgram of DNA, well within the acceptable levels for transfection experiments (Table 1).

TABLE 1

Colorimetric Endotoxin Assay of Purified Plasmid DNA

| | $A_{545}$ | [Endo-toxin] (EU/mL) | [plas-mid] (ng/µL) | Vol. Tested (µL) | [Endo-toxin] (EU/100 µL) | Plas-mid (µg) | [Endo-toxin] (EU/µg) |
|---|---|---|---|---|---|---|---|
| Spin column 1 | 0.486 | 0.17 | 183 | 100 | 0.017 | 18.3 | 0.0009 |
| Spin column 2 | 0.575 | 0.20 | 183 | 100 | 0.020 | 18.3 | 0.0011 |
| Pipette tip col. 1 | 0.526 | 0.19 | 76 | 100 | 0.019 | 7.6 | 0.0025 |

TABLE 1-continued

Colorimetric Endotoxin Assay of Purified Plasmid DNA

| | $A_{545}$ | [Endo-toxin] (EU/mL) | [plas-mid] (ng/μL) | Vol. Tested (μL) | [Endo-toxin] (EU/100 μL) | Plas-mid (μg) | [Endo-toxin] (EU/μg) |
|---|---|---|---|---|---|---|---|
| Pipette tip col. 2 | 0.477 | 0.17 | 76 | 100 | 0.017 | 7.6 | 0.0022 |
| Pipette tip col. 3 | 0.472 | 0.17 | 76 | 100 | 0.017 | 7.6 | 0.0022 |

Each bacterial cell contains approximately 2 million endotoxin molecules. For the larger scale preparations (maxi, mega and giga) endotoxin removal is more difficult. Because of the large volumes of bacterial culture processed (and the larger number of cells), the column resin is loaded quite heavily relative to the loading of the smaller columns. That is, the amount of endotoxin relative to the capacity of solid phase is greater. As a consequence, the final concentration of endotoxin in the purified DNA is somewhat higher. In these larger preparations, it is more difficult to obtain a concentration of 0.01 or less endotoxin units per microgram of DNA. A Maxiprep experiment yielded endotoxin concentrations of between 11 and 16 EU/μg.

Although the endotoxin concentrations were higher with the larger plasmid preparations, transfection frequency was still high. As a consequence, the term, "substantially endotoxin-free" is defined herein as an endotoxin concentration of less than 100 EU/μg.

Scale-Up to High-Throughput Midiprep

Another significant point of novelty of the instant invention is in the area of scale-up. Plasmid purification protocols are typically called "miniprep", "midiprep", "maxiprep", "megaprep" or "gigaprep" based on their scale and yield. Although these plasmid purification protocols are known in the art, an automated system for performing 96 midipreps at a time has not been described previously. In the instant application, scale-up to a high-throughput midiprep was achieved.

For the purpose of this invention, an automated miniprep method is defined as a method in which the amount of plasmid or nucleic acid recovered is in the range of up to 30 μg as shown in Table 2. A scale-up to midiprep was achieved so that 96 samples were processed simultaneously with a yield of plasmid DNA in the range of 20 to 200 μg. For a midiprep, the yield can be in the range having a lower limit of 20 μg, 25 μg or 30 μg and an upper limit of 50 μg, 60 μg, 80 μg, 100 μg, 120 μg, 140 μg, 160 μg, 180 μg or 200 μg. The cell lysate used for midiprep can be unclarified, clarified or partially-clarified.

TABLE 2

Comparison of miniprep in midiprep

| | Mini | Midi |
|---|---|---|
| Growth volumes | 1-5 ml | 2-30 mL |
| Resuspension buffer | 150 μL | 200 μL |
| Lysis buffer | 180 μL | 510 μL |
| Precipitation buffer | 210 μL | 300 μL (PB1) |
| | | 530 μL (PB2) |
| Column volume | 1 mL | 1 mL |
| Bed volume | 10-120 μL | 100-500 μL |
| Yield | up to 30 μg | 20-200 μg |

Scale-up to an automated, high-throughput midiprep cannot be considered case of optimization through routine experimentation or automating a manual procedure. Development of this parallel, automated midiprep procedure required a number of additional technical obstacles to be overcome. It was not possible to simply scale up the bed volume and reagent volumes used in the miniprep because of the volume constraints imposed by the use of 1-mL or 1.2-mL pipette tip columns To create an automated, high-throughput midiprep procedure, it was not possible to simply scale up the column bed volume and all the solution volumes proportionally. The midiprep plasmid purification requires a larger amount of resin in each column when compared to the miniprep columns. It was challenging to increase the bed volume while still leaving sufficient space in the column chamber for the solutions. The volume of the sample and other solutions used to process the sample increased dramatically. To make the invention compatible with commercial liquid handing systems and commercially-available pipette tips, a 1 mL pipette tip body was used. As a consequence, the combination of the column bed, sample and solutions were limited to 1 mL.

Spin columns are not subject to this problem for scale-up. For example, a commercially-available miniprep spin column has bed dimensions of 7.0 mm diameter and 2.05 mm height giving a bed volume of 79 $mm^3$. When the bed material is scaled up to midiprep size, the bed dimensions increase to 13.9 mm diameter and 11.2 mm height giving a bed volume of 1700 $mm^3$. This is more than a 20 fold increase in bed size.

In contrast to spin columns, with the pipette tip format, it wasn't possible to scale up the column bed volume 20-fold. The bed volume for the miniprep is 10-120 μL. Certainly, the bed size could be decreased if a lower recovery of plasmid is desired. But, if a larger yield of plasmid is required, it is not possible to increase the bed volume 20 fold as is the case with spin columns. If the volume of the 120-μL column bed were increased 20-fold, it would be 2.4 mL, a volume too large to fit in a 1-mL pipette tip. The pipette tips cannot hold enough medium for a 20-fold scale-up.

At the outset, it appeared to be impossible to scale the automated method enough to obtain 20-200 μg of purified plasmid because of these volume constraints. In commercially-available spin or gravity-flow columns, the volumes of the solutions are increased 15 to 20-fold when scaling up from miniprep to midiprep. Clearly, this was an added difficulty when scaling an automated method performed in a 96-well format. If the resuspension, lysis and precipitation buffers were scaled up 20 fold, the total volume would be over 10 mL. For bacterial growth, 2-mL deep well plates are the most common size for the 96-well format. It might be possible to use 4-mL deep-well plates however they are not readily available. Even with 4-mL plates, multiple wells would have to be used to contain the unclarified lysate.

Growth volumes can be adjusted depending on parameters such as the richness of the growth medium and the copy number and size of the vector. In one embodiment, cells for midiprep can be grown in a flask or tube. For example, a 30 mL of overnight culture can be processed by a single midiprep column. In another embodiment the starting culture is between 5-15 ml which produced approximately 50 μg of purified plasmid. With low density cultures or low copy number vectors, it may be desirable to process 30 mL of bacterial culture to get recoveries of greater than 50 μg of plasmid.

In some embodiments, growth for midiprep can be performed in multi-well plates. For instance, cells can be grown in 6-, 12-, 24-, 48- or even 96-well plates. When 96 midiprep columns are used and growth is performed in plates having fewer than 96 wells, multiple plates can be used for growth, (e.g., four, 24-well plates can be used to grow cells for 96 midiprep columns.) In these embodiments, the consolidation from e.g., 24-well plates to 96 columns can be performed with a liquid handing system. Alternatively, consolidation can be performed with a multi-channel or even a single-channel pipette.

Consider for example, cell growth in four 24-well plates for 96 midiprep columns. Consolidation from the 24-well plates to 96 columns can be performed at varying stages during processing. In one embodiment, cells can be transferred directly from the 24-well plates into one or more 96-well plates. In a second embodiment, the 24-well growth plates can be centrifuged, the growth medium can be decanted, resuspension buffer can be added and the cell pellet can be resuspended by gentle mixing with a liquid handling robot as described previously. In this embodiment, the resuspension buffer volume can be chosen to yield the desired volume of resuspended cells. That is, a small volume of resuspension buffer can be used to produce a highly-concentrated cell suspension.

During development of the automated midiprep, one of the first problems tackled was the size of the column bed. It was preferred that the bed size not be too large because of limited chamber space above the bed. In certain embodiments, the bed volume is less than half the volume of the pipette tip in which the column is made. In these embodiments the bed volume can be less than ⅓ the volume of the pipette tip or less than ¼ of the pipette tip volume. It is desirable to have considerable space above the bed so that relatively large liquid aliquots can be processed by back and forth flow.

It is also possible to use a bed volume that is greater than half the volume of the pipette tip in which the column is made. This is not preferred however for several reasons. First, a larger bed would give rise to higher resin costs. Second, a larger bed would result in a larger volume of eluted plasmid which could require further concentration, e.g., by ethanol precipitation. Third, because the resin would take up as significant portion of the column volume, it would be necessary to process smaller liquid aliquots during the capture and wash steps.

In one experiment, a 300 μL resin bed in a 1 mL pipette tip was tested. This bed height was 3.75 times higher than the miniprep columns (80 μL resin bed) described herein. In another experiment, the column bed volume was 400 μL. Experiments were performed in which enough cell lysate was passed through the column to load the columns to capacity. Surprisingly and unexpectedly, it was discovered that the resin did have enough capacity to recover up 100 μg of plasmid. Without wishing to be bound by theory, the significant increase in plasmid yield may have been due to the porous nature of the packing material. Nevertheless the results were unexpected. The column bed size for midiprep recovery of 20-200 μg nucleic acid recovery ranged from 85-800 μL, 200-500 μL or 300-400 μL. In certain embodiments, the bed volume for a midiprep was in the range of 100 μL to 500 μL.

The bed size can also be defined by the percentage of the pipette tip column taken up by the bed. For example, an 85 μL bed in a 1.2-mL pipette tip takes up approximately 7% of the volume available in the tip. Therefore, the bed size for a midiprep can take up at least 7%, at least 8%, at least 12%, at least 16%, at least 20%, at least 25%, at least 29% or at least 33%, of the volume available in the tip.

Although it is the most economical to manufacture the columns from commercially-available pipette tips, it is also possible to make columns that can engage a liquid handler but are cylindrical in shape, or even another shape. In these embodiments, the resin can take up a smaller percentage of the tip.

Next, the volume constraints of the resuspension buffer, the lysis buffer, the precipitation buffer and the entire sample were examined. A smaller volume of resuspension buffer could be used with the consequence that the cell suspension would be more concentrated. A more concentrated cell suspension would give rise to a more concentrated lysate. Since the lysate is unclarified in some embodiments of the invention, a more concentrated lysate has more particulates, more cell debris and more genomic DNA per unit volume, making it more difficult to process.

Alternatively, a larger volume of resuspension buffer could be used and the sample could be captured from multiple wells, perhaps up to 4 or more. However, the larger volumes are more difficult to work with and would require additional disposables and expense. In one embodiment, the midiprep procedure employs 4 mL resuspension buffer, 4 mL lysis buffer, and 6 mL of precipitation buffer, making the total volume 14 mL. A volume of 14 mL would require 8 wells of a 96-well deep-well block. So while this embodiment would be possible to automate, it is not optimal.

In order to solve this issue, several smaller resuspension, lysis and precipitation buffer volumes were tested to reduce the total volume we need to process the midi sample:
1. 300 μL Resuspension buffer, 300 μL Lysis buffer, 410 μL Precipitation buffer: total=1010 μL
2. 500 μL Resuspension buffer, 500 μL Lysis buffer, 700 μL Precipitation buffer: total=1700 μL
3. 1 mL Resuspension buffer, 1 mL Lysis buffer, 1.4 mL Precipitation buffer; total=3.4 mL
4. 2 mL Resuspension buffer, 2 mL Lysis buffer, 2.8 mL Precipitation buffer: total=6.8 mL These volumes may be adjusted to produce more concentrated reagents. However, this may produce more particulate or the salts and buffers making up the reagents may become insoluble at the concentrations required by the process. A range of reagent concentrations up to, and including those concentrations listed in Table 3 can be used in the automated midiprep procedure.

In some embodiments, more concentrated neutralization/precipitation reagents can be used by performing the neutralization in two steps. That is, the guanidine hydrochloride could be added prior to the potassium acetate or vice versa. In certain embodiments, these reagent concentrations can also be used in the automated miniprep procedure. In other embodiments, the precipitation buffer can be omitted and the capture step can be performed following addition of the lysis buffer.

TABLE 3

Midiprep buffers

| Buffer Name | Content |
|---|---|
| Resuspension buffer | 1M Tris-HCl pH 8.0, 1M EDTA, 4 mg/mL RNase A |
| Lysis buffer | 6M NaOH, 10% SDS |
| Precipitation, buffer | 10M guanidine hydrochloride 5M Potassium acetate pH 4.5 |
| Wash buffer | 1M TRIS-HCl pH 7.5, and up to 100% Ethanol |

In some embodiments, the ratio of resuspension buffer to lysis buffer to precipitation buffer is considered. This ratio can be 1:1:1.2. In certain embodiments, less resuspension buffer is used in order to minimize the total volume. That is, the ratio of resuspension buffer to lysis buffer can be 1:1 or it can be less. For example, 150 µl of resuspension buffer can be used with 500 µl lysis buffer. When this small volume of resuspension buffer is used, the buffer can be 10-fold more concentrated. Alternatively, 300 µl or 500 µl resuspension buffer can be used with 500 µl Lysis buffer.

In certain embodiments, the resuspended cells can be transferred to a 96-well plate for further processing. However, it is also possible to continue processing in the 24-well format. Cell lysis and precipitation can be performed in the 24-well format, and the aqueous portion of the resulting unclarified lysate can be processed on a midiprep column.

In many embodiments, the plasmid is captured by repeated aspiration and expulsion through the open lower end of the midiprep column. In other embodiments, the sample can be applied to the open upper end of the midi column and allowed to pass through the column by vacuum or gravity flow.

When capture is performed by repeated aspiration and expulsion, partial sampling of the unclarified lysate can be used as described above. In one embodiment, partial sampling can be performed in several aliquots. After each aliquot is processed, it can be expelled to waste.

As with the miniprep, the wash and elution steps can be done with aspiration and expulsion or they can be done by using by gravity flow. When aspiration and expulsion are used, the buffers can be delivered in a top-down fashion (from above) or a bottom-up fashion (from a well below the column).

The 96-well automated method can be performed with clarified, partially-clarified or unclarified lysates.

Scale-Up to Automated Maxi, Mega and Gigaprep

In another aspect of the invention, it is possible to automate larger yield plasmid preparations. To do this, it is necessary to scale up the bacterial culture volume, the column size, the column bed volume and the buffer volumes respectively. Example volumes and yields are shown in Table 4.

It should be noted that the plasmid purification methods and devices described herein are not limited to the cell ranges listed in table 4. It is also possible to process fewer cells. In fact, it is possible to process between $1.3 \times 10^{11}$ and $5 \times 10^{12}$ cells. By the same token, it is possible to prepare plasmid DNA from fewer than $1.3 \times 10^{11}$ cells.

Bacterial cells grown rich media can yield relatively concentrated cultures in the range of $10^9$ to $10^{13}$ cells per mL of growth medium. For example, the concentration of bacterial cells can be greater than $10^9$ cells per mL of growth medium, greater than $2 \times 10^9$ cells per mL, greater than $4 \times 10^9$ cells per mL, greater than $6 \times 10^9$ cells per mL, greater than $8 \times 10^9$ cells per mL, greater than $10^{10}$ cells per mL, greater than $10^{11}$ cells per mL or greater than $10^{12}$ cells per mL of growth medium.

The concentration of bacterial cells the culture can also be expressed in terms of pellet wet weight per liter of culture. The pellet wet weight per liter of culture can be in the range of 1-21 g/L, 1-7 g/L or 4-21 g/L. Stated another way, the pellet wet weight per liter of culture can be greater than 3 g/L, greater than 4 g/L or greater than 5 g/L.

In some embodiments, it is possible to scale up to a teraprep. In these embodiments, the growth volume is larger than 3 L, on the order of 8-12 L, columns would be 50-100 mL, bed volumes would be 20-40 mL and yield would be 12-60 mg.

TABLE 4

Comparison of maxiprep, megaprep and gigaprep

| | Maxi | Mega | Giga |
| --- | --- | --- | --- |
| Growth volumes | 30-500 mL | 90-1500 mL | 1.5 L-3 L |
| Pellet wet weight | 2-14 g | 6-32 g | 12-64 g |
| Number of cells | $5 \times 10^{12}$-$5 \times 10^{13}$ | $1.5 \times 10^{13}$-$1.5 \times 10^{14}$ | $3 \times 10^{13}$-$3 \times 10^{14}$ |
| Resuspension buffer | 5-80 mL | 25-350 mL | 100-500 mL |
| Lysis buffer | 5-80 mL | 25-350 mL | 100-500 mL |
| Precipitation buffer | 5-80 mL | 25-350 mL | 100-500 mL |
| Column volume | 20 mL | 20 mL | 2 × 20 mL |
| Bed volume | 1.5-5 mL | 3-10 mL | 3-10 mL |
| Yield | 0.5-1.5 mg | 1-4 mg | 3-15 mg |

Because of the larger column size, the throughput is lower than that of midiprep. However the system is largely automated nevertheless.

The plasmid preparation procedure can be performed as follows.
1. Grow culture overnight.
2. Transfer bacterial culture into tubes or bottles and centrifuge to pellet cells. Decant the medium.
3. Add resuspension buffer to the pelleted cells. Resuspend cells completely to obtain a cell suspension.
4. Add lysis buffer to the cell suspension and mix to produce a cell lysate.
5. Optionally, add precipitation buffer to the cell lysate and mix.
6. Optionally, transfer the cell lysate to a filtration apparatus and passed the cell lysate through the filter.
7. Transfer the lysate or filtrate to tubes, wells or reservoirs on the instrument deck.
8. Capture the lysate on a column.
9. Pass one or more wash buffers over the column.
10. Optionally transfer the columns to the drying station and pass air through the column.
11. Add elution buffer to column.
12. Recover purified plasmid.

Bacterial cultures can be grown in any of the media described above. In certain embodiments, cultures are grown in a rich medium such as Terrific Broth. In some embodiments, cells are grown in a medium that is not LB.

After growth, the cells are transferred to centrifuge tubes or bottles, centrifuged and the growth medium is discarded, leaving the cell pellet. The cell pellets can be frozen at this stage and plasmid DNA can be purified at a later date or time.

In some embodiments, steps 3 through 6 can be performed manually. In these embodiments of the invention, the automated steps begin during filtration and include capture, wash and recovery of the plasmid. These automated steps may take between 15 minutes and 360 minutes depending on the number of samples, scale of each sample, capture duration and the extent of washing needed.

In alternate embodiments, the procedure can be automated from step 3. Cells can be resuspended by the instrument (which is described below) in an automated fashion. Buffers can be added by the instrument and mixing can be accomplished in an automated fashion, e.g. by repeated aspiration and expulsion through a pipette tip. In these embodiments, a wide-bore can be used for mixing the sample in steps 4 and 5 and for transferring the lysate to the filtration apparatus in step 6.

When steps 3 to 6 are performed manually, the cells can be resuspended by a number of means including vortexing, shaking or pipetting.

Particles such as beads can be combined with the cell pellet and the resuspension buffer to aid resuspension. These particles can agitate the mixture through direct physical contact with the cells during shaking, vortexing, stirring, etc. to break up the cellular pellet. Particle materials include glass, plastic, metal, polymers, minerals and mixtures of these materials. Metal particles can include transition metals and mixtures containing iron and alkaline earth metals. These particles can be spherical or have any other shape. When the particles are spherical, their diameter can be in the range of 0.1 mm to 15 mm. When the particles are not spherical, their size can be measured on the longest side or face. The volume of particles used can be expressed as a percentage of the volume of the resuspension buffer and can be in the range of between 1% and 20% of the resuspension buffer volume. The actual volume of particles used can also be in the range of 2 mL to 20 mL.

The use of particles for resuspension is unorthodox, novel and non-obvious for several reasons. First, there is the danger that the particles will lyse some of the cells prematurely. Second, the particles might sheer the genomic DNA. Sheared genomic DNA can co-purify with the plasmid DNA. When purified plasmid DNA is contaminated with genomic DNA, the contaminating genomic DNA cannot be removed. Third, glass and some metals (such as transition metals and alkaline earth metals) and plastics can bind DNA which could negatively impact plasmid yield.

The buffers used for maxi, mega and gigaprep are similar to those disclosed herein for miniprep and midiprep. The resuspension buffer is typically comprised of TRIS, EDTA and RNase a however in some embodiments, the resuspension buffer can also be comprised of a sugar or salt. The lysis buffer is usually comprised of a surfactant such as SDS. The concentration of surfactant in the lysis buffer can be greater than 1%. In terms of ranges, the concentration of surfactant to is in the range of 0.8% to 3%, 0.9% to 2.8%, 1% to 2.7% or 1.1% to 2.6%. The precipitation buffer can contain a chaotrope such as guanidinium HCl. The concentration of guanidinium can be in the range of 3 to 6 molar or 3.5 to 5.5 molar.

The addition of lysis buffer and precipitation buffer can be performed manually by pouring or pipetting or the addition of these buffers can be automated e.g., with a liquid handling instrument. In certain embodiments, the precipitation buffer can be chilled.

After the addition of the lysis and precipitation buffers, the samples can be mixed in any way including manually inverting, stirring, gentle mixing or automated methods such as pipetting up and down. In some embodiments, the precipitation buffer is omitted and filtration can be performed following the lysis step.

For capture, wash and elution, liquids can be passed through the column in any manner including gravity, pressure, vacuum and aspiration/expulsion. The liquids can be delivered to the column bed in a top-down fashion (from above) or a bottom-up fashion (from a well, tube or reservoir below the column).

When filtration is performed, a filtrate is produced during step 6. The cell lysate can be manually poured into the filtration apparatus. If this step is automated, the cell lysate can be transferred to the filtration apparatus using a pipette such as a wide-bore pipette or by a valving and tubing apparatus.

It can be desirable to perform incubation steps during the plasmid preparation procedure. Incubation steps can be performed at any point during plasmid purification however, it may be particularly desirable to perform an incubation after steps 4, 5 or 11. When incubation is performed, it can be 30 minutes or less. That is, the incubation step may be performed for approximately 1 minute, 2 minutes, 3 minutes, 4 minutes, 5 minutes, 6 minutes, 7 minutes, 8 minutes, 9 minutes 10 minutes. 15 minutes, 20 minutes, 25 minutes or approximately 30 minutes. When incubation is less than 1 minute, the incubation duration can be 3 seconds, 5 seconds. 10 seconds, 20 seconds, 30 seconds, 40 seconds or 50 seconds.

In other embodiments, the incubation duration can be longer than 10 minutes. In fact, the procedure can be paused between some operation steps.

The cell lysate from step 5 can be transferred to a filtration apparatus on the instrument deck to remove (or partially remove) particulates such as cell debris. If beads or particles were added to resuspend the cell pellet, they will be filtered and removed from the lysate at this step. This step is optional. If the filtration apparatus is not used, several alternatives are possible. (1) Plasmid can be purified directly from an unclarified lysate. (2) A clarified lysate can be produced by centrifugation. (3) The lysate can be filtered via a different means such as pressure or vacuum.

When the filtration apparatus is used, the precipitated sample is partially filtered using a large-pore filter. In these embodiments, partial filtration can be performed by gravity flow. However, in alternative embodiments, partial filtration can also be performed using vacuum, centrifugation or pressure.

In certain embodiments, the particulate can be filtered completely to remove substantially all particulates from the cell lysate. In these embodiments, a clarified lysate can be produced by, pressure, filtration or centrifugation. Plasmid DNA can be captured from the clarified lysate in the same manner as the partially clarified lysate or the unclarified lysate. In still other embodiments, and unclarified lysate can be used. That is, the cell lysate can be processed without filtration or centrifugation.

During filtration, portions or aliquots of the filtrate can be removed from the filtration apparatus in an automated fashion and transferred to a reservoir or container on the instrument deck. These aliquots can then be passed through the column in an automated fashion while the filtration step is still ongoing. In other embodiments, the filtration step is completed before the capture step begins.

In some embodiments, the column can be a modified pipette tip. The columns are described in more detail below. The filtrate can be applied to the column bed in a top-down fashion or a bottom-up fashion. When the filtrate is applied to the column in a bottom-up fashion, it can be aspirated and expelled (through the open lower end of the column) one time. In other embodiments, the filtrate is repeatedly aspirated and expelled.

The filtrate or cell lysate volume can be larger than the column volume. In certain embodiments, the filtrate is applied to the column in multiple aliquots. That is, the column can be loaded multiple times and large volumes of filtrate can be processed through the column. For example, a first aliquot of the filtrate or cell lysate can be passed through the column followed by a second aliquot. The first aliquot can be aspirated and expelled through the open lower end of the column one time. A portion of the plasmid DNA in the first aliquot is captured on the solid phase within the column and the liquid flows to waste. In this example, the column volume can be 20 mL in the volume of the first aliquot is less than 20 mL. In some embodiments, the aliquot volume is in the range of 1 mL to 15 mL. In these embodiments, the aliquot volume can be 10 mL.

Multiple aliquots can be passed through the column in this manner. After the first aliquot is passed through the column, a second aliquot can be passed through the column followed by a third aliquot, etc. Each aliquot can be passed through the column a single time or the aliquot can be passed through the column repeatedly.

In certain embodiments, the filtrate may be added to the capture column in a continuous or semi-continuous manner. That is, the filter apparatus can be positioned in line with the column and filtrate could flow directly from the filter apparatus into the capture column The instrument described herein can be programmed to perform any sequence of capture and wash steps. In some embodiments, a wash solution is passed through the column between each lysate aliquot while in other embodiments, several aliquots are passed through the column before the wash solution. In one example, two aliquots of filtrate can be aspirated and expelled through the pipette tip column one time followed by a wash step. In another example, three aliquots of filtrate are aspirated and expelled through the pipette tip column a single time followed by a wash step. In alternative embodiments, each aliquot is passed through the pipette tip column multiple times.

The wash can be performed with one or more buffers to remove proteins and other contaminating material not of interest from the column. The column may be washed once or several times with different buffers. The wash can be performed using top-down, bottom-up or back and forth flow.

In some embodiments, after the column is washed, air can be passed through the column to remove bulk liquid and/or organic solvent such as alcohol. This can be accomplished by depositing the pipette tip columns onto a drying station or vacuum block and passing air through the columns. A vacuum block adaptor or drying station was custom built for this process and is integrated into the instrument deck. The drying station is described in more detail below. In other embodiments heated air can be pushed through the column or the column itself can be heated to remove bulk liquid. In still other embodiments, air can be pushed and then pulled through the column.

Depending on the scale of the plasmid preparation or the nature of the wash buffers, air can be passed through the pipette tip columns for a duration of up to 60 minutes or more. That is, air can be passed through the columns for 0 minutes, to 5 minutes, up to 10 minutes, up to 15 minutes, up to 20 minutes, up to 25 minutes, up to 30 minutes, up to 40 minutes, up to 50 minutes or up to 60 minutes. Stated in terms of ranges, air can be passed through the columns for between 0 minutes and 60 minutes, between 5 minutes and 55 minutes, between 10 minutes and 50 minutes or between 20 and 40 minutes.

Stated in other terms, air can be passed through the samples until the solvent remaining on the column is below a particular threshold. For example, air can be passed through the columns and tell until the amount of organic solvent (e.g. ethanol) is less than 5% or less than 3%.

After washing, the plasmid is eluted to recover the purified plasmid. The elution/desorption solution may be a buffer or water. In certain embodiments, the elution buffer is heated. It can be added to the column in a top-down or bottom-up fashion. In some embodiments, the desorption solution is incubated on the column prior to elution. The incubation duration can be up to 30 minutes or even longer. The purified plasmid can be recovered in a vial or tube.

Multiple samples can be processed in parallel. In some embodiments of the instrument, between 1 and 24 columns can be automatically processed in parallel. In other embodiments of the instrument, it is possible to process between 2 and 12 columns or between 2 and 6 columns in an automated fashion.

Instrument for Maxiprep, Megaprep and Gigaprep

The invention described herein includes an automated apparatus or instrument capable of large-scale automated plasmid preparation. This instrument can perform most or all steps of the plasmid purification process in an automated fashion using computer or automatic control. In general, the instrument performs timed events in a predetermined sequence. Once initiated, the timing and sequence of events cannot be changed. This means the process must be robust and versatile enough to be able to process samples that vary in composition and volume.

Hardware and firmware were combined to create an instrument capable of automated plasmid preparation at the maxiprep, megaprep and gigaprep scales. The instrument is able to recover plasmids at three different scales without modification. This is remarkable because the range of the number of cells in a sample that can be processed spans a range greater than 100.

The instrument is comprised of a pumping means. At least two pumps or channels are used for liquid handling. In certain embodiments, the pumps are pipette heads that can engage pipette tips for liquid handling and pipette tip columns for plasmid capture and purification. In some embodiments, the instrument can contain three, four or more channels that can operate in parallel to purify plasmid DNA from two or more bacterial cultures processed in parallel.

In other embodiments, the pumps are not pipettes. In these embodiments, the pumps can engage a column.

An instrument comprised of two pumps can perform up to 4 maxipreps, up to 4 megapreps and up to 2 gigapreps. That is, plasmid DNA can be purified from up to 4 different samples at the maxiprep and megaprep scales and up to 2 different samples at the gigaprep scale.

Columns, reagents, buffers, filters and containers are arranged on a deck of an instrument or automated apparatus that has x, y and z motion. Samples, columns and liquid reagents can be moved in the x, y and z directions.

This flexibility of the instrument for handling multiple plasmid preparation scales can be accomplished using a uniform column size and column engagement circumference for maxiprep, megaprep and gigaprep. The column engagement circumference is defined herein as the distance around the column that seals the column to the instrument. The column may be engaged to a pipetting head, a pump or a vacuum, all of which can be used to process liquids through the column. The circumference may be any shape including circle, square, rectangle, polygonal, etc. For example, in some embodiments of the instrument, the column volume is 20 mL and the bed volume can range from 0.5 mL up to 15 mL. However, if larger or smaller columns are used, the size and shape of the upper end of the column remains consistent so that that no major modification of the instrument is needed to engage columns of varying sizes. The column volume may be up to 5, 10, 20, 40, 50, 75, or 100 mL and larger.

In some embodiments, the column body volume is 20 mL but the column bed volume can vary depending on the scale of the plasmid preparation. The instrument can engage columns of different bed sizes without modification of the instrument itself or the instrument head used to engage the columns. This engagement seals the vacuum or pressure needed to force liquid flow through the column.

For 20 mL columns, the engagement circumference is 6.3 cm. However, the instrument may operate using different size columns. Engagements circumferences can be in the range of 0.5, 1, 2, 4, 6, 8, 10, 12, 14, 16, 18, 20, 25, 30, 35, 40, 50 or 60 cm. The engagement diameter is related to the column diameter.

After the bacterial culture is pelleted by centrifugation and the resuspension buffer has been added, the instrument can resuspend the cells. This resuspension function can be integrated into the instrument and can be accomplished by a number of methods including vortexing, shaking, stirring, pulsed force (e.g. a disruptive shockwave) and sonication.

Buffers can be added to a sample via the liquid handling function. In some embodiments, wide bore pipette tips can be used for buffer additions and mixing.

In some embodiments, a column may be engaged directly or indirectly with the valve at the bottom of the filter apparatus receptacle. In these embodiments, automation can begin at the filtration step or before.

A 20-mL pipette tip column can be used for the maxi, mega and gigapreps. Because of the larger column size, it is not possible to perform 96 preparations simultaneously. Nevertheless, it is possible to automate the procedure. In some embodiments, the preparations may be performed in parallel for between 2 and 24 samples or more, depending on the scale.

Solutions and buffers on the instrument deck can be contained in any vessel. In certain embodiments, solutions are held in small reservoirs such as conical tubes (e.g. 25-100 mL). The instrument sample containers, filter container, filter, buffer containers, columns, and collection vials can be disposable. Additionally, the instrument can accommodate large buffer reservoirs on the order of 50, 100, 200, 300, 400, 500 mL, 1 L, 2 L, 3 L, 4 L or more.

The instrument has a drying station for passing air through the columns following the wash step and prior to elution. In some embodiments of the instrument, the drying station can serve as an integrated vacuum which can be used for any step of the plasmid purification process including filtration, capture, wash and elution.

Filtration, capture, column washing and plasmid DNA elution can all be performed in an automated fashion. As the instrument is scaled up along with the liquid handling volumes, gripping can be more of an issue. Several strategies can be used to prevent or control dripping from liquid handling pipette tips, pipette tip columns or other columns. First, the instrument can utilize smooth acceleration and deceleration in the X, Y and Z directions. Second, drip lanes can be incorporated into the instrument deck design. That way, if drips do occur, they will not fall into crucial spots on the instrument deck such as samples or reservoirs. Third, the instrument deck can be designed in such a way that the pipetting head does not need to travel very far between method steps. Fourth, to minimize dripping, it is possible to aspirate and airgap prior to moving a filled pipette tip, pipette tip column or other type of column.

Figure 7:
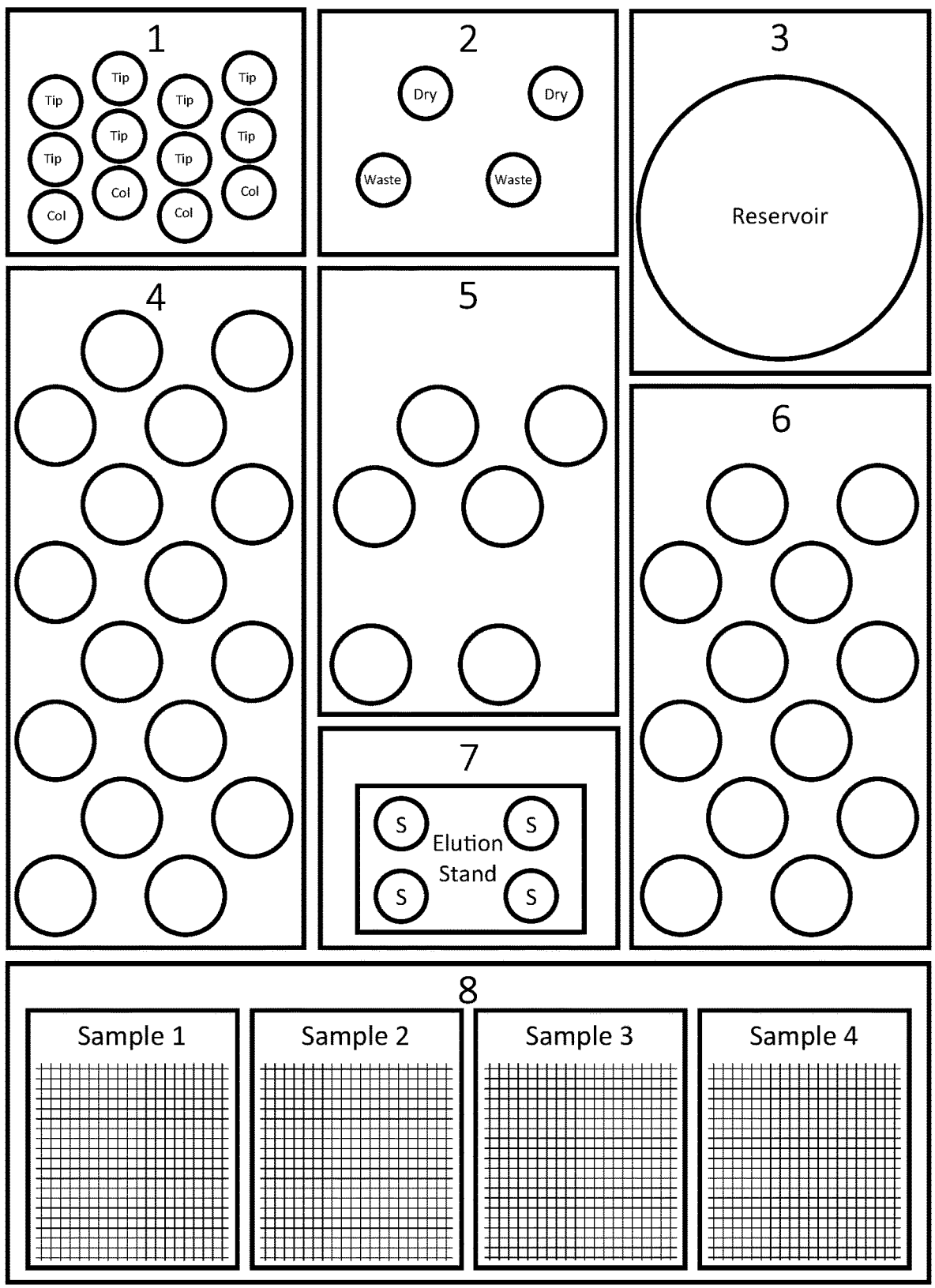
FIG. 7 depicts one embodiment of the instrument deck.

One embodiment of the instrument deck is shown in FIG. 7. The instrument deck is divided to 8 different sections. The four rectangles in section 8 are filter apparatuses. These can also be called sample processing plates. Cell lysates are filtered or partially filtered in section 8 after which the filtrate is transferred to conical tubes in section 4. The filtrate is captured on columns in section 1. Also in section 1 are transfer tips (pipette tips for liquid handling). When two or more wash buffers are used, one wash buffer is contained in the reservoir in section 3 while the other wash buffers can be placed in section 5. Section 5 is also available for any supplemental buffers which may be needed. Section 6 can also be used for reagents and buffers. After the wash step, air can be passed through the columns in section 2. Purify plasmid DNA can be eluted in section 7.

The Challenges of Automation and Scale-Up

Automation removes the drudgery of performing operations manually. However, automation is generally restrictive because there is no opportunity to change or adapt a method to problems that arise during operation. For example, in manual plasmid preparation methods that use filtration, the timing of the various steps is subject to change depending on the amount of cell debris a particular sample. Because the length of time necessary to achieve filtration may vary, it is difficult to automate this step.

It was quite challenging to design an instrument capable of processing three different scale preparations. The computer control was difficult to implement because the timing of each step must be predictable and reproducible. The timing of events controlled by computer software and firmware must be determined. If timing for the various steps of the processes are unpredictable or uncontrollable, it is challenging to create an automatic process control in which a sequence of predetermined times are used to perform the progression of events.

Failure of an automated method can occur for a number of reasons. For example, failure can be due to the sheer number of cells that require processing as the method is scaled up. Indeed, as the scale of a plasmid prep is increased, the amount of cell debris or flocculent that must be processed also increases, which in turn increases the problem of computer timing. Increasing the number of cells in the sample increases the flocculent that must be filtered before the plasmid is captured. But there are limitations on the amount of material that can be filtered, especially in an automated instrument. In addition, an instrument that performs different scales of plasmid preparation must accommodate a wide range of cell flocculent mass amount. The instrument must be flexible and the duration of each step must be predictable to operate successfully under conditions in which the amount of cell flocculent changes dramatically.

When a process is automated, it becomes less flexible and more limited because programmed events are performed in a predetermined inflexible manner. However, the instrument described herein is capable of three different scales of plasmid preparation: maxiprep, megaprep and gigaprep.

There are several barriers to automating maxiprep, megaprep and gigaprep plasmid purifications. This is especially true for developing a device and method that can operate any or all three of these plasmid preparation scales, with the large amounts of particulates and reagent volumes. It is remarkable that an instrument can purify plasmid DNA from samples in which the number of cells differ by 100-fold or more.

It is particularly difficult to automate the filtration step. Samples that are prepared from large culture volumes filter at different rates. The flow rate of a lysate through a filter differs from one sample to the next due to differences in the suspension content. Even within the filtering of one particular sample, the rate of filtering will change or slow unpredictably as the filtering process proceeds. This slow down during filtration may be due to filling or plugging of the pores of the filter with particulate. In some extreme cases the filtering rate may even stop if the amount of particulate applied to the filter is too high. Thus, the time it takes to filter any particular sample will vary widely for any filter and method whether it is gravity, pressure or vacuum filtering. This variation within a sample in between samples makes it difficult to program the filtering duration which in turn, makes it difficult to program the next step process which is capture.

When a filtering method is performed manually, adjustments can be made based on visual examination of the filtering process. These adjustments are usually time-based adjustments. One simply waits for as long as it takes for the filtering process to be completed. However, pressure or vacuum filtering methods may also be adjusted for difficult samples, as determined visually. Thus, it is routine to compensate for differences between samples when performing the purification with a manual method. Manual methods are laborious however, they can be easier to perform successfully. The only caveat is the sample type and volume must remain within parameters specified by the design of the manual kit. If the sample is not within these parameters, then even manual intervention may not be enough to keep the sample flow moving.

One problem is that filters within automated devices methods can plug. The pores of the filter can fill with particulate at different rates depending on the quantity of particulate in the suspension. As the pores fill, the flow rate of the lysate through the filter will decrease. Although still functioning, the ability of the filter to remove particulates will decrease as some pores become clogged. This makes it difficult to process cells from a range of culture volumes because the amount of particulate in the lysate as well as the concentration can vary. For example, an automated filter system that works for a maxiprep may not work well for mega- and gigaprep purifications. Likewise, an automated filter system that works for megapreps may not work well for maxipreps or gigapreps.

Automating the capture step is also challenging. Plasmid capture rates vary based on a number of parameters. Samples are captured by the medium within the column at different rates so capture conditions have to change for samples that have a wide range of capture volumes. The medium can be comprised of a membrane or particulate solid phase capable of plasmid DNA capture. There may be a wide range of plasmid concentrations in various filtrates. High concentrations of plasmids promote faster and more complete capture, but low plasmid concentrations from low yielding cultures are difficult to capture on the stationary phase. Capture is less complete and is a longer process. The variable time required for capture for samples makes it difficult to program the capture time and capture conditions to cover the range of possible plasmid concentrations and volumes. A column capture system that may operate in an automated instrument built to perform a maxiprep may not function effectively for the larger megaprep and gigaprep scales, especially in an automated system. A column system that is scaled to megaprep may not function at the maxiprep and gigaprep scales, especially in an automated system.

It is challenging to automate the wash step. The wash step removes contaminants that are not specifically bound to the solid phase. Depending on the particular sample, the amount and the concentration of these contaminants can vary over a wide range. The column wash may have to be performed to different extents depending on the contaminants present in a particular sample. This is especially true for stationary phases that have relatively high surface areas because they can bind genomic DNA and contaminants present in the lysate. Thus, predicting through a programed automated instrument the conditions for washing is difficult. A column wash system that operates effectively in an automated instrument that is scaled to a maxiprep may not function at mega and gigaprep scale, especially in an automated system. Likewise, a wash system that is scaled to megaprep may not function at maxi and gigaprep scale and a wash system that is scaled to a gigaprep may not function at mega and gigaprep scale.

In contrast to automated methods, manual methods such as gravity or vacuum can be monitored visually and the duration of each step can be adjusted accordingly. These manual steps take different amounts of time depending on the sample volume, concentrations, particulate, etc. The methods of manual operation depend on being able to adapt and change the timing of the steps and possibly other parameters such as the volumes of the buffers, the chamber volumes of the column and the vials, etc.

These challenges to automating the protocol for large scale plasmid preparation are compounded when two or more samples are processed in parallel. The variation between samples amplifies the challenges described above. Samples filter at different rates so it is difficult to time. Samples capture at a different rate so capture conditions may differ between the two parallel samples. There can be a range of capture volumes. Particulates can plug the filter for one sample, but not another. There can be a wide range of plasmid concentrations in the filtrates, making capture uneven. There are a wide range of contaminants in filtrate making the column wash different for samples performed in parallel depending on the contaminants present in a particular sample.

It is difficult to pre-determine the speed any of the processes such as filtering. One sample will always be different from another. Interestingly, this may be why there is a limit on how many manual processes can be run in parallel. There must be constant attention to the individual sample preparations. The manual steps always take different amounts of time depending on the sample. The methods of manual operation depend on being able to adapt and change the timing of the steps. When it's necessary to visually monitor each sample, the number of samples that can be run in parallel is limited.

A number of strategies were employed to meet the challenges faced by automation of large scale plasmid purification. First, the methods and devices of the invention utilize rapid, yet effective filtering. The filtering device uses a large surface area of greater than 3 cm$^2$ which can be effective for gravity, pressure and vacuum filtering. It is unusual to use such a large surface area filter in an automated instrument. Additionally, the pore size of the filter can be 10 μm or more. This large pore size is also unorthodox because some of the particulate in the lysate can flow through the filter. The combination of a large surface area filter and the use of a large pore size makes the filtration process efficient in terms of the time needed. The filtrate can be collected quickly and completely.

The device is able to filter lysate rapidly within each class of plasmid preparation, maxiprep, megaprep and gigaprep. For a maxiprep, the filtration step can take between 1 and 30 minutes. For a megaprep or a gigaprep, the filtration step can take between 3 minutes and 60 minutes.

Second, a capture strategy can be used that allows processing of large volumes of filtrate. The receiving chamber of the filtration apparatus can be large and aliquots of filtrate can be removed from the filtration apparatus during the filtration process. The capture process can be started even before the filtering process is completed. That is, during the filtration step, aliquots of filtrate can be removed from the filter apparatus and captured on the column. In this manner, the volume of the filtrate can be quite a bit larger than the column chamber volume. In addition, filtration can be ongoing during the capture. This strategy of utilizing simultaneous capture and filtration provides some compensation for the variation of filtration speed between samples that are being processed in parallel. Even when samples vary significantly in their filtering speed, the timing of the capture step can accommodate the slowest filtering sample.

Third, an instrument programming strategy can also help automate large scale plasmid purification. A different program is used for each scale, maxiprep, megaprep and gigaprep. Within a scale, the duration of each step including capture, washing, drying and elution is set to the longest length of time anticipated for that step. The column bed size also varies for maxiprep, megaprep and gigaprep. Yet the column hardware (inlet, outlet, frits and column chamber) is compatible and can communicate in the device and method of the instrument with the capture column bed volumes ranging in size from 0.2-20 mL.

Fourth, the instrument deck can also be designed in a way that aids automated large scale plasmid purification. Two or more wash buffers can be added sequentially to the column after the capture step. The columns are solvent addressable. Sample and buffer containers can be accessed by the column or by a liquid handling function. Samples and liquids can be added to the top of the column or aspirated through the open lower end of the column. The volume of reservoirs capture containers allow for a range of buffer volumes that can be used for each plasmid preparation scale. Tubes and reservoirs used with the instrument can have volume ranging from 0.5 mL to 5 L.

The Columns

In the subject invention, a bed of medium is contained in a column that has an open upper end and an open lower end. The bed of medium is held in place with a bottom frit positioned near the open lower end of the column. In some embodiments, the columns are additionally comprised of a top frit. Non-limiting examples of suitable columns, particularly low dead volume columns are presented in U.S. Pat. No. 7,482,169. It is to be understood that the subject invention is not limited to the use of low dead volume columns. The columns may be configured into plates or racks or used individually.

Typically, the column is comprised of a column body having an open upper end, an open lower end, and an open channel between the upper and lower ends of the column body; a bottom frit extending across the open lower end and a bed of medium positioned inside the open channel above the bottom frit.

Figure 1:
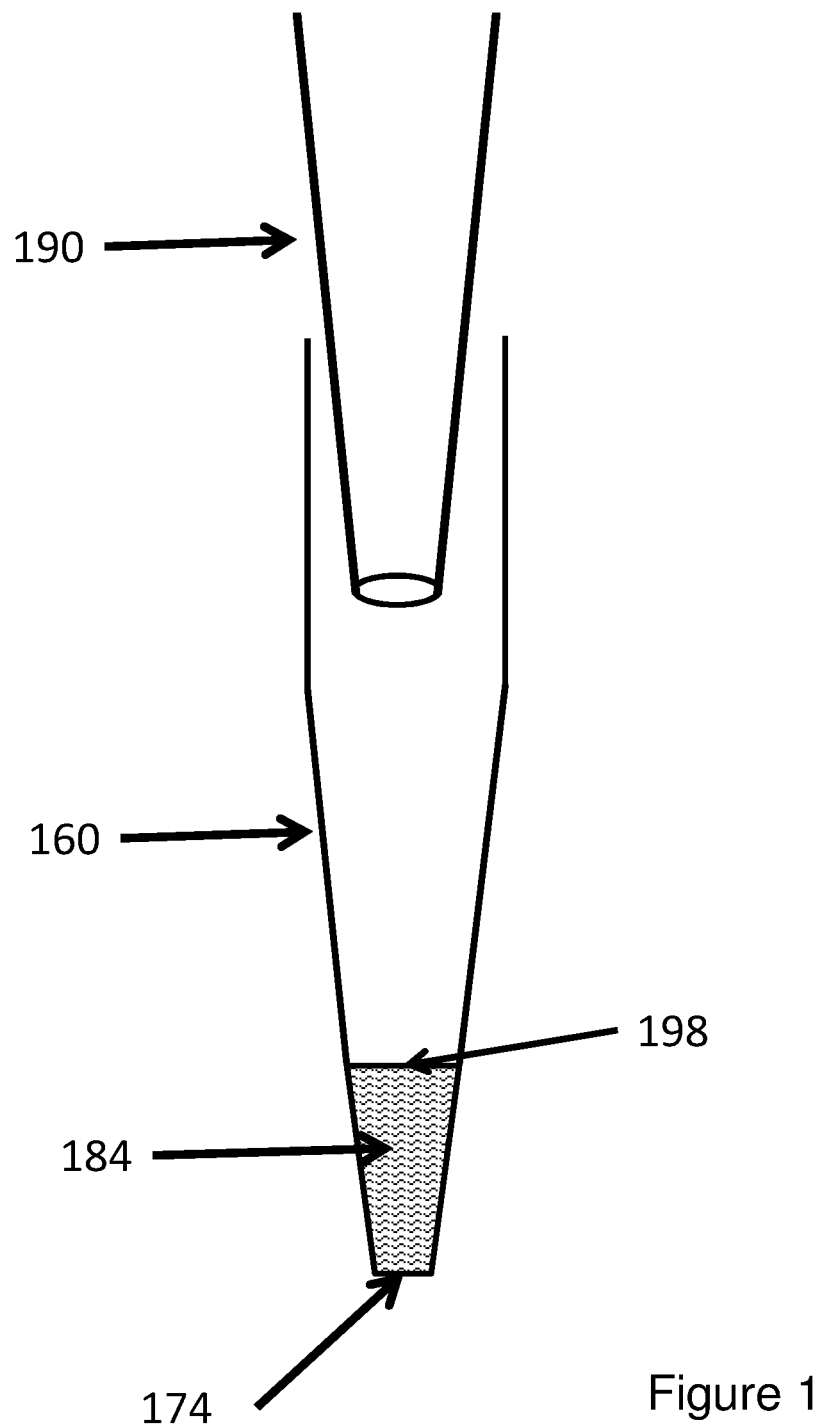
FIG. 1 depicts an embodiment of the pipette tip column.

In certain embodiments, the column body is comprised of a pipette tip. FIG. 1 depicts an embodiment of pipette tip column construction. Disposable pipette tip 160 is cut at the lower end and frit 174 is welded to the lower end of the tip body. A silica resin 184 was transferred into the tip. In certain embodiments, upper frit 198 is placed above the resin, e.g., using a friction fit. Pipette tip 190 can engage the liquid handling system used to process the columns.

The columns will have some backpressure due to the bed of medium and the frit(s). The backpressure of a column will depend on the average bead size, bead size distribution, average bed length, average cross sectional area of the bed, backpressure due to the frit and the viscosity and flow rate of the liquid passing through the bed.

Similar to the midiprep, the column bed size can be characterized by the percentage of the pipette tip column taken up by the bed. For the maxi, mega and gigaprep, the percentage of the column that is occupied by the solid phase is in the range 4% to 55%.

Column Media

Because the invention is directed to the purification and/or concentration of nucleic acids, extraction surfaces capable of adsorbing such molecules are particularly relevant. The chemistry employed in the present invention is typically based on normal phase or ion-exchange. Ion-pairing may also be used for nucleic acid purification. In general, these chemistries, methods of their use, appropriate solvents, etc. are well known in the art.

The media or solid phase used in the column can be a form of water-insoluble particle (e.g., a porous or non-porous bead, fiber or other particle) that has an affinity for the nucleic acid of interest. Silica beads are suitable for the columns of the invention. Silicon quartz is large well. Davisil 923 and 635 work well. Other suitable materials include celite, diatomaceous earth, silica gel, silica gel, (Davisil, Impaq, Biotage), metal oxides and mixed metal oxides, glass, alumina, zeolites, titanium dioxide, zirconium dioxide. Ion exchangers made of inorganic or polymeric substrates also work quite well.

The beads or particles used in the column have a shape or pore structure that provides a large surface area or exposed surface. In some embodiments, the capture material has a surface area of greater than 0.5 m$^2$, 1 m$^2$, 1.5 m$^2$, 2 m$^2$, 3 m$^2$, 5 m$^2$, 6 m$^2$, 10 m$^2$, 20 m$^2$ or 30 square meters per gram of material.

The bed volume of the medium used in the columns of the invention depends on the scale of the plasmid purification but it is typically in the range shown in tables 2 and 4. In certain embodiments, the bed volume can be in the range of 0.2 mL to 20 mL. In terms of percentage, the bed volume can be in the range of 5% to 50% of the column volume. In certain embodiments, the bed volume can be in the range of 7%-40% of the column volume or in the range of 10%-30% of the column volume.

The space between resin particles can also be important. This space increases with looser packing of the column. In certain embodiments, the column beds are not tightly packed.

In other embodiments, the plasmid DNA can bind to a membrane such as a silica membrane in the column. DNA binds to silica in the form of particles, beads, gels or fibers. Membranes may consist of fibers or a mixture of particles and fibers. Silica may be bound with a binding agent to form a membrane. The materials may be packed as particles into columns or formed as membranes and then placed into columns. Membranes are porous so that liquids can pass through the column.

Ion exchange resins can also be used for plasmid purification. Although it is not always the case, some anion exchange resins are used in gravity-flow, liquid chromatographic columns containing porous silica beads or other types of polymer or inorganic base media modified with diethylaminoethanol or another strong or weak base anion exchanger. Any anion exchange group may be used. Anion exchange bed volumes can be larger than the bed volumes used in silica-based columns.

Frits

One or more frits is used to contain the bed of medium in a column. Frits can take a variety of forms, and can be constructed from a variety of materials. The frits of the invention are porous, since it is necessary for fluid to be able to pass through the frit. The frit should have sufficient structural strength and integrity to contain the extraction media in the column. It is desirable that the frit have little or no affinity for chemicals with which it will come into contact during the extraction process, particularly the analyte of interest. Frits of various pores sizes and pore densities may be used provided the free flow of liquid and particulates is possible. Frits of pore size large enough to prevent plugging from cell debris are of particular interest. Some frits of the invention have a large pore size frit.

In one embodiment, a single frit (e.g., a lower, or bottom, frit) extends across the open channel of the column body. Often, the bottom frit is attached at or near the open lower end of the column, e.g., extending across the open lower end. This configuration is not required, i.e., in some embodiments, the bottom frit is located at some distance up the column body from the open lower end. Normally, a bed of medium is positioned inside the open channel in contact with the bottom frit.

In certain embodiments, a top frit may be employed. For example, in some embodiments, a second frit extends across the open channel between the bottom frit and the open upper end of the column body. In this embodiment, the top frit, bottom frit and column body (i.e., the inner surface of the channel) define a media chamber wherein a bed of medium is positioned. The fits should be securely attached to the column body and extend across the column body to completely occlude the channel, thereby substantially confining the bed of medium inside the media chamber.

In some embodiments, the top frit can be just above the bed of medium or in contact with the bed of medium. In other embodiments, the top frit is positioned well above the medium, e.g., 25 mm or more above the medium in a 200 μl pipette tip column or 50 or more mm above the bed in a 1.2-mL pipette-tip column. The position of the top frit can be proximal to open upper end of the pipette tip column. That is, the top frit can be closer to the open upper end of the column than to the bed medium. In these embodiments, the bed is not packed and the medium can occupy well under 50% of the volume of the extraction media chamber and the top frit can be significantly thicker than the bottom frit. In some embodiments, liquids may not flow through the top frit.

The position of the top frit over the bed may just touch the top of the resin bed or be positioned substantially above the resin bed. When the frit is above the resin bed, the resin bed may move or expand with aspiration of liquids including the sample containing the particulates. The bed may move down against the bottom frit with expulsion of the liquid.

The performance of the column is typically enhanced by the use of frits having pore or mesh openings sufficiently large to allow cell debris or other particulates to flow through the frit without clogging or plugging under low pressures applied by a pipette or liquid handler. Of course, the pore or mesh openings of course should not be so large that they are unable to adequately contain the extraction media in the chamber. Frits used on columns of the invention can have pore openings or mesh openings of a size in the range of about 5-500 μm, more preferably 10-200 μm, and still more preferably 100-150 μm, e.g., about 120 μm.

In some cases, it is necessary to consider the relationship between the frit pore size and the particle diameter. Specifically, it is possible to increase the frit pore size when the particle diameter is increased. For example, a frit pore size of 100 μm was used successfully with a range of different resins.

Some embodiments of the columns of the invention employ a thin frit, preferably less than 2000 μm in thickness (e.g., in the range of 20-2000 μm, 40-350 μm, or 50-350 μm), more preferably less than 200 μm in thickness (e.g., in the range of 20-200 μm, 40-200 μm, or 50-200 μm), more preferably less than 100 μm in thickness (e.g., in the range of 20-100 μm, 40-100 μm, or 50-100 μm). However, thicker frits, up to several mm, 5 and even 10 mm, thick may be used if the pore size of the frit can be increased dramatically.

Some embodiments of the invention employ a membrane screen as the frit. The use of membrane screens as described herein typically provide this low resistance to flow and hence better flow rates, reduced backpressure and minimal distortion of the medium. The membrane can be a woven or non-woven mesh of fibers that may be a mesh weave, a random orientated mat of fibers i.e. a "polymer paper," a spun bonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the sample and various processing liquids through the column bed, may be attached to the column body, is strong enough to withstand the bed packing process, is strong enough to hold the column bed of beads, and does not interfere with the extraction process i.e. does not adsorb or denature the sample molecules.

The frit can be attached to the column body by any means which results in a stable attachment. For example, the screen can be bonded to the column body through welding or gluing. The column body can be welded to the frit by melting the body into the frit, or melting the frit into the body, or both. Alternatively, a frit can be attached by a friction fit or by means of an annular pip, as described in U.S. Pat. No. 5,833,927.

The frits of the invention can be made from any material that has the required physical properties described herein. Examples of suitable materials include polymer, sintered polymer, fiber, nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, vinyl polymer, metal (e.g., steel), ceramic and glass.

In certain embodiments of the invention, a wad of fibrous material is included in the column, which extends across the open channel below the open upper end of the column body, wherein the wad of fibrous material and open channel define a media chamber, wherein the medium is positioned within the media chamber. This wad of fiber can be a porous material of glass, polymer, metal, or other material having large pores. In some embodiments, the wad of fibrous material is used in lieu of an upper frit.

Solvents

Disruption of bacterial cells is typically accomplished using an alkaline solution containing a detergent. Any detergent that effectively disrupts the cell membrane can be used for this purpose. In other embodiments, the lysis procedure is mechanical or physical. In some methods, the lysis procedure involves treatment with a surfactant.

The lysis procedure is usually followed by the addition of a neutralizing solution (also known as a precipitation solution).

The neutralization solution may contain an acid. It may also contain a chaotropic agent and/or other components In certain embodiments of the invention, chaotropic agents can be added to the sample prior to nucleic acid capture. A chaotropic agent is a molecule in water solution that can disrupt the hydrogen bonding network between water molecules (i.e. it exerts chaotropic activity). This has an effect on the stability of the native state of other molecules in the solution, mainly macromolecules (proteins, nucleic acids) by weakening the hydrophobic effect. Chaotropes can be complexed with an alcohol or a salt. Examples of chaotropic reagents include sodium iodide, sodium perchlorate, guanidine thiocyanate (GuSCN), urea, guanidine hydrochloride (GuHCl), potassium iodide, sodium perchlorate, potassium chloride, lithium acetate, lithium chloride, magnesium chloride, sodium chloride, butanol, ethanol, phenol, propanol, sodium dodecyl sulfate, thiourea, urea or mixtures of such substances. These chaotropes may have other properties. For example, butanol and ethanol are solvents. Sodium dodecyl sulfate is a surfactant.

Chaotropic agents can be used to retain plasmids on the column medium or to wash contaminants from plasmids already captured on the column. Chaotropic agents may be used in conjunction with solvents or salts to retain plasmids on the column medium or to wash contaminants from plasmids captured on the column. Solvents include butanol, isopropyl alcohol and ethanol, all of which are alkyl alcohols. Salts may include sodium acetate or potassium hydrogen phosphates: all common water soluble salts.

Examples of suitable solvents for use with the invention are shown in Tables 5 and 6.

TABLE 5

| | Normal Phase Extraction | Normal Phase Chaotropic Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | chaotropic buffers alcohol | $H_2O$, buffers, ion-pairing reagent |
| Typical desorption solvent | Ethyl acetate, acetone, $CH_3CN$ (Acetone, acetonitrile, isopropanol, methanol, water, buffers) | $H_2O$/buffer | $H_2O/CH_3OH$, ion-pairing reagent $H_2O/CH_3CN$, ion-pairing reagent (Methanol, chloroform, acidic methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease chaotropic buffer | Decrease solvent polarity |

TABLE 6

| Desorption Solvent Features | Ion Exchange Extraction | Hydrophobic Interaction Extraction | Affinity Phase Extraction |
|---|---|---|---|
| Typical solvent polarity range | High | High | High |
| Typical sample loading solvent | $H_2O$, buffers | $H_2O$, high salt | $H_2O$, buffers |
| Typical desorption solvent | Buffers, salt solutions | $H_2O$, low salt | $H_2O$, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase | Decrease ionic strength | Change pH, add competing reagent, |

TABLE 6-continued

| Desorption Solvent Features | Ion Exchange Extraction | Hydrophobic Interaction Extraction | Affinity Phase Extraction |
|---|---|---|---|
| | retained compounds pH or decrease pH | | change solvent polarity, increase heat |

Methods for Using the Columns

The method involves capturing nucleic acids on pipette tip columns. The method can be performed in parallel and can be automated. Prior to the capture step, the columns are usually wetted with an equilibration solution. After capture, the columns are washed to remove non-specifically bound material. Then the nucleic acids are released from the column in an elution step.

In certain embodiments of the method, the open upper end of the column is operatively engaged with a pump and the sample, wash and/or desorption solvents are aspirated and discharged through the open lower end of the column. Often, aspirate/expel steps are repeated multiple times, i.e., a plurality of in/out cycles can be employed to pass the solvent back and forth through the bed more than once. In other embodiments, fluids enter the column through the open upper end and exit the column through the open lower end.

A pump can be used to pass liquids through the column. Alternatively, liquids can be passed through the column by gravity flow or vacuum. In other embodiments, the capillary action can be used to wick solvents upward through the open lower end of the column.

The invention provides a pipette or pipettor (such as a multi-channel pipettor) suitable for acting as the pump in methods such as those described herein. In some embodiments, the pipettor comprises an electrically driven actuator. The electrically driven actuator can be controlled by a microprocessor, e.g., a programmable microprocessor. In various embodiments, the microprocessor can be either internal or external to the pipettor body.

In preferred embodiments of the invention, a plurality of columns is operated in a parallel fashion, e.g., multiplexed. Multiplexing can be accomplished, for example, by arranging the columns in parallel so that fluid can be passed through them concurrently. When a pump is used to manipulate fluids through the column, each column in the multiplex array can have its own pump, e.g., syringe pumps activated by a common actuator. Alternatively, columns can be connected to a common pump, a common vacuum device, or the like.

In certain embodiments the pipettor is a multi-channel pipettor. In other embodiments, a robotic system such as those commercially available from Dynamic Devices, Zymark, Hamilton, Beckman, Tecan, Packard, Matrix, PhyNexus, Agilent and others are used for nucleic acid purification. In some embodiments, robots having a 96-channel pipetting head are utilized. In some embodiments, a robot with an 8-channel or a 12-channel pipetting head is used.

In certain embodiments, throughput is maximized by performing some steps with bidirectional flow and other steps by unidirectional flow including the use of vacuum, pressure or gravity. For example, the capture step can be performed using bidirectional flow and the wash and elution steps can be performed using vacuum or gravity flow. In these embodiments, the pipetting head of the robotic liquid handler can be utilized more efficiently for simply dispensing liquids, allowing a greater number of columns to be processed in parallel. It is also possible to perform the capture, wash and elution steps using gravity or vacuum.

The invention also provides software for implementing the methods of the invention. For example, the software can be programmed to control manipulation of solutions and addressing of columns into sample vials, collection vials, for spotting or introduction into some device for further processing.

During aspiration and expulsion, the lower end of the pipette tip column can be positioned relatively close to the tube or well bottom, e.g., within a range having a lower limit of about 0.05 mm, 0.1 mm, 0.2 mm, 0.3 mm, 0.4 m, 0.5 mm, 1 mm, 2 mm, 3 mm, 4 mm, or 5 mm from the bottom of the well, and an upper limit of 0.3 mm, 0.4 m, 0.5 mm, 1 mm, 2 mm, 3 mm, 4 mm, 5 mm, 6 mm, 7 mm, 8 mm, 9 mm or 10 mm of the well bottom. For example, in some embodiments the open lower end of a pipette tip column is positioned with between 0.05 and 2 mm from a well bottom, or between 0.1 and 1 mm from a well bottom. The term "well bottom" does not necessarily refer to the absolute bottom of a well, but to the point where the tip makes contact with the well when the tip is lowered to its full extent into the well, i.e., a point where the tip can seal with the well surface. For example, in some microwell plate formats the wells taper down to an inverted conical shape, so a typical tip column will not be able to make contact with the absolute bottom of the well.

The invention also includes kits comprising one or more reagents and/or articles for use in a process relating to solid-phase extraction, e.g., buffers, standards, solutions, columns, sample containers, etc.

Nucleic acids and particularly plasmids can be purified from any source including eukaryotic or prokaryotic cells, tissues, body fluids (blood, serum, plasma, saliva, urine, feces), tissue culture, bacteria, viruses. The purification procedure can be used with low, medium or high copy number plasmids. The instant invention can also be used to isolate nucleic acids from a gel.

The Drying Station

The methods of the instant invention utilize a drying station. The terms, drying station, drying block, vacuum manifold and vacuum block are used interchangeably herein. The drying station allows air to be passed through the pipette tip columns. Some commercially-available DNA preparation methods utilize vacuum manifolds. However, these manifolds are designed only to pull liquid through columns or plates. Common formats for these manifolds are 24-column and 96-column capacity. Since these existing manifolds are open underneath the columns or plates, it is often necessary to monitor liquid flow through the different columns to ensure the liquid has passed through all the columns. The drying station described herein differs from commercially available vacuum manifolds. While manifolds are designed mainly to pull liquid through columns, the drying station allows prolonged airflow distributed evenly over all the columns.

One embodiment of the drying station block is shown in FIGS. 2 and 3. In contrast to existing manifolds, the channels within the block completely surround each column. In certain embodiments, the channels surround each column over substantially the entire length of the column. This design ensures liquid and air flow is comparable between columns.

In other embodiments, the drying station can be designed with a channel that surrounds each column but not over the entire length to form a seal with the pipette tip column, primarily at the lower end of the column.

Vacuum or airflow applied to the drying station can be controlled by software so that it occurs at the appropriate time and for the appropriate duration.

Figure 2A:
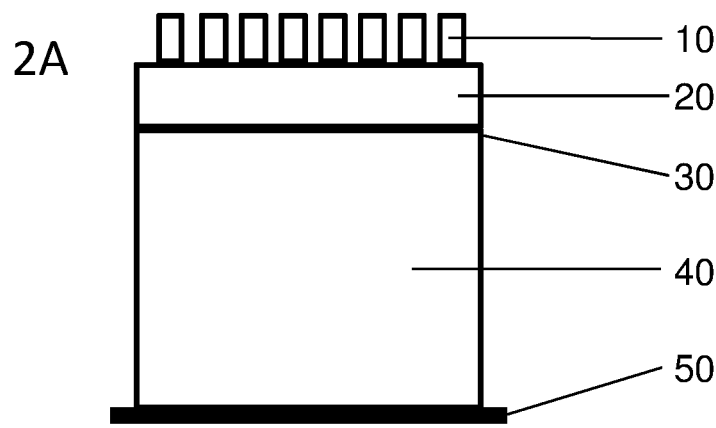
FIGS. 2A-2C depict an embodiment of the drying station with front and side views.
Figure 2B:
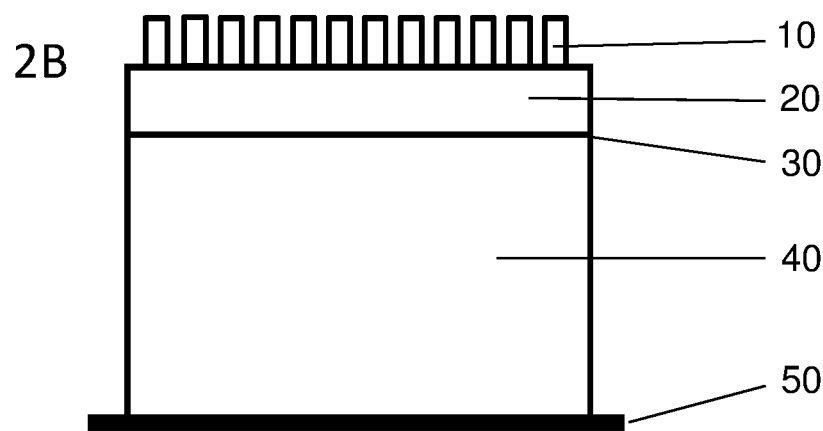
Figure 2C:
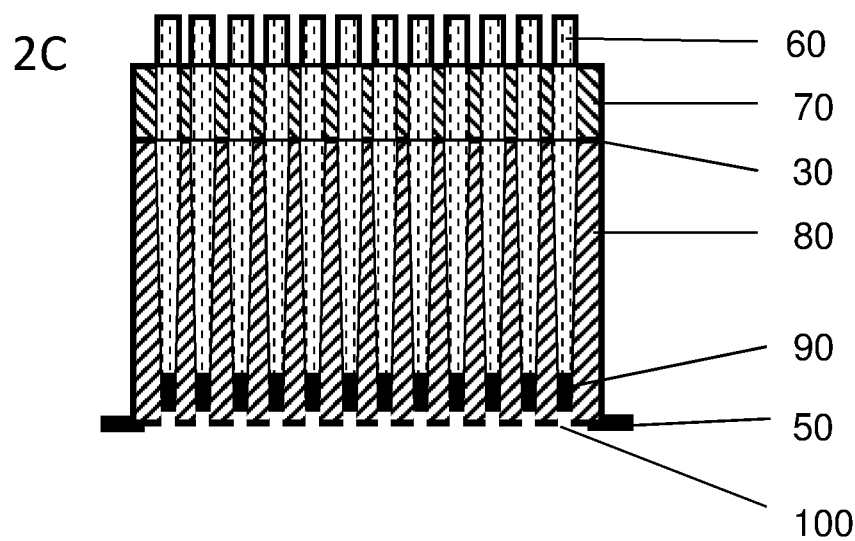
Figures 3A, 3B:
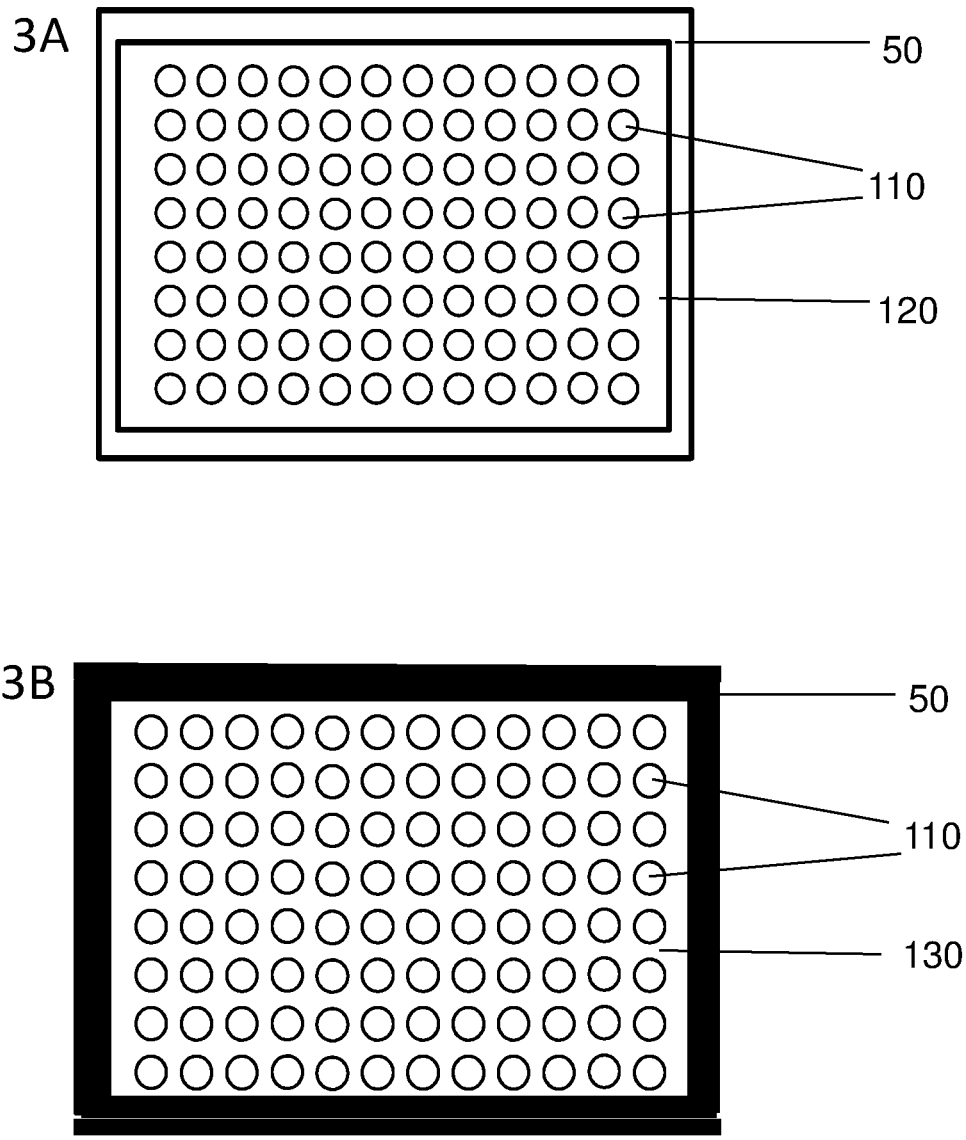
FIGS. 3A-3B depict an embodiment of the drying station block with top and bottom views.

FIGS. 2A-2C depict embodiments of the side and front views of the drying station and FIGS. 3A-3B show the top and bottom of the block. In this embodiment, the block contains positions for 96 columns. In other embodiments, the block may contain positions for any number of columns including for example, 1, 2, 3, 4, 5, 6, 8, 12, 24, 48 or 384 columns.

FIG. 2A depicts an embodiment of the side view of the adapter block, the tops of eight columns 10 are inserted into top block 20. Top block 20 is separated from bottom block 40 by sealing gasket 30. The gasket forms a seal around each individual column when they are inserted into the block so that the airflow is applied through the columns and not around the sides of the column bodies. The bottom of bottom block 40 contains plastic lip 50. In this embodiment, the lip conforms to SBS standardized format for 96-well plates so that the base of the block can be inserted into the vacuum manifold or any deck position of a robotic liquid handler.

FIG. 2B depicts the front view of the drying station block pictured in FIG. 2A. It is identical to the side view shown in view A except that the row of twelve columns 10 can be seen.

FIG. 2C is a cut-away view of the drying station front view. Pipette tip columns 60 are exposed to show that when inserted into the block they extend almost to the bottom. In this embodiment, the end of the column does reach the bottom of the vacuum block. In other embodiments, the lower ends of the columns will be even with the bottom of the drying station block. In still other embodiments, the ends of the columns will extend out past the base of the vacuum block. Opening 100 allows the vacuum to be applied at the bottom of the block and allows liquid and air passage through the columns sealed by gasket 30. Cross section of top block 70 is separated from cross section of bottom block 80 by gasket 30. In certain embodiments, the column shape is frustoconical and the holes at the interface of top block 70 and bottom block 80 have a smaller diameter than those on the upper surface of top block 70. The nucleic acids are captured from the sample by column packing material 90, and then washed and eluted.

FIG. 3 depicts and embodiment of the top view of the drying station and FIG. 3B shows the bottom view of the vacuum block. Lip 50 lies at the bottom of the block near bottom surface 130. Pipette tip columns are inserted into through holes 110 from top surface 120.

In an alternative design, the drying station block lacks a gasket. Even without a gasket, the pipette tip columns are in sealing engagement with the block. In this design, the block can be one solid piece or can be comprised of multiple pieces.

Genomic DNA Isolation

The method for purification of plasmid DNA from a cell culture was modified for purification of genomic DNA. Genomic DNA can be extracted and purified from any cell type including bacteria, plants and animals. Examples of different cell types include mouse tail, blood, saliva, tissues from biopsies, cerebrospinal fluid, animal tissues, plant tissue and whole organisms such as fruit flies, worm and embryos. Genomic DNA isolation can be performed in a completely automated fashion in 96-well format. The same automated procedure can also be used when fewer than 96 samples are processed. Small footprint liquid handling systems such as the PhyNexus MEA can perform the purification process.

To purify genomic DNA, the sample is transferred to individual wells of a 96-well deep well plate in preparation for lysis. Typically, between 5 and 100 mg of sample is used. Often, the amount of sample is between 10 and 50 mg.

In certain embodiments, proteinase K can be added to the sample to generate a more homogeneous sample. This is particularly advantageous for tissue samples. Even with the addition of proteinase K, the sample is still considered an unclarified lysate. After the addition of proteinase K, the sample may contain particulates or it may be liquid. It is remarkable that genomic DNA can be isolated directly from a sample without removing the solid components.

After lysis, the sample can be incubated. In some embodiments, the sample is heated during the incubation step, while in other embodiments, incubation is performed at room temperature. Room temperature is defined here in as between 20 and 30° C. In those embodiments in which the sample is heated, the incubation can be carried out at temperatures between 35 and 100° C. More specifically, the incubation can be performed at between 40 and 90° C. and often, the incubation is performed at temperatures between 45 and 55° C.

When the incubation step is performed, the duration can be between 1 and 20 hours. Liquid samples such as blood may require a shorter incubation period, in the range of 5-90 minutes. To perform a heated incubation using automation, deep well plates can be moved from room temperature positions to heating positions using a robotic arm.

Next, RNase A can be added to each sample and the samples can be incubated. Again, the samples can be incubated at room temperature or, a higher or lower temperature can be used. Incubation times can be very short, (minutes) or longer (hours).

Bacterial samples can be lysed as described above. For tissue samples, lysis can be carried out using similar reagents and conditions to those used for bacterial cells. Among other ingredients, lysis buffers can contain buffers such as Tris, salts (e.g., NaCl), chelators such as EDTA, and detergents such as SDS and surfactants such as CTAB (Cetyltrimethylammonium bromide). In some embodiments, two different lysis buffers can be used in sequence. After addition of the lysis buffer, the samples can be incubated for varying times and temperatures, depending on the sample type. For example, the samples can be incubated at 50-90° C. for 5-30 minutes. In other embodiments, the sample is not heated and is incubated at room temperature. Prior to loading the sample on the column, an alcohol such as ethanol can be added to the samples.

There is no requirement for centrifugation and the viscous samples can be quite viscous. Nevertheless, they can be purified with pipette tip columns. Unlike the procedure for purification of plasmid DNA, the genomic preparation procedure does not require a precipitation step. The genomic DNA must be kept in solution in order to extract it with the pipette tip columns. In the plasmid purification method described above, the genomic DNA is precipitated to remove it from solution. However, in the genomic DNA method, the precipitation buffers are omitted to keep the genomic DNA accessible for the pipette tip column.

The pipette tip columns can be equilibrated on the head of the MEA or another instrument. The pipette tip columns can then be equilibrated with water or buffer.

To capture genomic DNA, the pipette tip columns can be unloaded into a drying station on the MEA instrument. The MEA can then use pipette tips to add the sample to the top of the resin bed and passage of the sample through the pipette tip column can be achieved by gravity or by applying a vacuum. In alternative embodiments, the sample is aspirated through the open lower end of the pipette tip column and the capture step can be performed with back and forth flow.

Depending on the sample type, it may be desirable to perform incubation steps at different stages during the purification procedure as described above. For example, an incubation can be performed after treatment with proteinase K, after lysis, or after treatment with RNase A. Incubations can be performed at an appropriate temperature and for an appropriate duration.

After the capture step, a wash step can be performed although in some embodiments, the wash step is omitted. Wash buffers are typically comprised of water, buffers, alcohols and combinations thereof. As with the capture step, the wash can be performed with unidirectional or bidirectional flow. The pipette tip columns can be loaded onto the MEA pipetting head and washed using bidirectional flow. In some methods a pause is incorporated after each aspirate step and/or after each expulsion. The alcohol concentration can be in the range of 60-100%. The wash can be repeated with fresh wash buffer for one, two or more additional washes.

After the wash, the columns can be transferred to the drying station and alcohol is removed from the bed of the pipette tip columns by flowing 1-500 cubic liters of air through the pipette tip column. The genomic DNA can then be eluted in a volume of elution buffer, typically in the range of 50-500 µL. The elution buffer can be aspirated into the column through the lower end or added from the upper end of the column. The elution buffer is typically comprised of water or buffer. In certain embodiments, the elution buffer is incubated on the column for several minutes prior to dispensing the purified DNA. For example, the incubation step can be performed for a period of between 1 and 20 minutes.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Evaluation of an 80 µLt Bed Volume Pipette Tip Column Containing a Resin for Purification of Plasmid from Eukaryotic Cells In this example, the performance of 80 µL bed volume pipette tip columns is evaluated. The pipette tip column was constructed from a 200 µL pipette tip (Tecan) and is packed with a silica-based particle resin. These columns, buffer conditions and column processing procedures are tested for the recovery of plasmid DNA from yeast. The yield and quality are assessed by UV spectrometry and agarose gel electrophoresis.

Samples are prepared by growing a single yeast colony in 25 mL medium supplemented with the appropriate carbon source to propagate the DNA vector. The liquid culture is incubated at 30° C. with shaking until the culture becomes turbid. The culture is divided into equal aliquots and subjected to centrifugation at 5,000×g for 15 minutes to pellet the yeast. The supernatant is discarded and the pellets are lysed by mortar and pestle, using liquid nitrogen and resuspended in buffer.

To purify the plasmid DNA from the lysed yeast cells, the pipette tip columns are processed by the ME semi-automated purification system (PhyNexus, Inc., San Jose, Calif.). The columns are equilibrated with 200 µL 7M guanidinium-HCl by performing one cycle of back-and-forth flow at 500 µL/min and a 20 second pause at the end of the aspirate and dispense steps.

The yeast lysate is subjected to pipette tip column processing for capture of the plasmid DNA by using at least 24 back-and-forth cycles at a flow rate of 250 µL/min with 20 second pauses after the end of each aspirate and dispense step.

Following plasmid capture on the pipette tip column, the columns are washed with 200 µL wash 1 buffer consisting of 10 mM Tris-HCl pH 6.6, 5M guanidinium-HCl and 30% ethanol. This is followed by a second wash in wash 2 buffer consisting of 10 mM Tris-HCl pH 7.5 and 80% ethanol. Both wash procedures are carried out using one cycle of back-and-forth flow at a flow rate of 500 µL/min with 20 second pauses at the end of each aspirate and expel step. A blow out step is incorporated to remove all residual wash buffer from the resin bed.

DNA plasmid is released from the column with 300 µL elution buffer consisting of water. The procedure to release the DNA is 8 back-and-forth cycles at a flow rate of 250 µL/min with 20 second pauses after the end of each aspirate and dispense step.

Example 2

Purification of Plasmid DNA from *E. coli*

Columns and methods for purifying plasmid DNA from *E. coli* lysate were developed for 96 samples at a time. The columns used in this example were 80 µL bed columns fitted with 100 µm pore size screen bottom fits. The method was designed to operate on a Tecan EVO, Biomek FX or other robotic liquid handler. The solutions used are listed in Table 7.

*E. coli* cells were grown to late logarithmic phase, harvested by centrifugation and then resuspended in buffer. The plasmid purification procedure developed was as follows.

1. Add 250 µL of Lysis buffer to resuspended cells using gentle pipette mixing for 3 minutes.

2. Add 350 µL of Neutralization buffer to lysed culture using gentle pipette mixing for 3 minutes.

3. Attach plasmid DNA pipette tip columns to 96 channel head.

4. Equilibrate the pipette tip columns by cycling through the equilibration buffer.
   Use 2 cycles at 0.5 mL/min flow rate.
5. Capture the plasmid DNA.
   Use 24 cycles at 0.25 mL/min flow rate.
6. Wash (Wash1 buffer, 500 µL) the captured plasmid DNA.
   Use 2 cycles at 0.5 µL/min flow rate.
7. Wash (Wash2 buffer, 500 µL) the captured plasmid DNA.
   Use 2 cycles at 0.5 µL/min flow rate.
8. Wash (Wash2 buffer, 500 µL) the captured plasmid DNA.
   Use 2 cycles at 0.5 mL/min flow rate.
9. Blowout remaining wash buffer.
10. Elute the captured plasmid DNA.
    Use 16 cycles at 0.25 mL/min flow rate.

The yield was approximately 5 µg per well. The purity was examined with agarose gel electrophoresis and UV absorption with $A_{260}/A_{280}$ ratio between 1.8 and 2.0.

Example 3

Purification of Plasmid DNA from *E. coli* Pellets

Columns and methods for purifying plasmid DNA from *E. coli* lysate were developed for 96 samples at a time. The columns used in this example were 80 µL bed columns fitted with 100 µm pore size screen bottom fits. The method was designed to operate on a Tecan EVO, Biomek FX or other robotic liquid handler. The solutions used are listed in Table 7.

*E. coli* cells were grown to late logarithmic phase, harvested by centrifugation and then resuspended in 150 µL Resuspension Buffer (50 mM Tris-HCl pH 8.0, 10 mM EDTA, 400 µg/mL RNase A). The plasmid purification procedure was performed as follows.

Using wide bore pipette tips, 150 µL of Lysis buffer (200 mM NaOH, 1% SDS) was added to the resuspended cells using gentle pipette mixing. Next, the precipitation step was carried out by the addition of 210 µL of precipitation Buffer (0.9 M potassium acetate pH 4.8, 4.2 M guanidinium hydrochloride) to lysed cells using gentle pipette mixing. The wide bore pipette tips were discarded and the liquid handling robot attached plasmid DNA pipette tip columns to the 96-channel head. The pipette tip columns were equilibrated in 500 µL of water with back-and-forth cycling of the equilibration buffer. A typical cycle consists of aspiration of 180 µL at a flow rate of 0.5 mL/minute followed by a pause of about 30 seconds while maintaining the end of the plasmid DNA pipette tip columns at the bottom of the well of a deep well or microplate. The second half of a cycle consists of dispense of 180 µL at a flow rate of 0.5 mL/minute followed by a pause of about 30 seconds while maintaining the end of the plasmid DNA pipette tip columns at the bottom of the well of a deep well or microplate. The plasmid DNA pipette tip columns next capture plasmid from the prepared *E. coli* samples using 14 cycles at 0.25 mL/min flow rate with 20 second pauses. After plasmid capture, the plasmid DNA pipette tip columns were blotted onto absorbent lab paper by to remove cell debris and precipitants. The DNA pipette tip columns next went through wash by submerging the end of the column on 500 µL of Wash Buffer (100 mM Tris-HCl pH 7.5, 65% ethanol) using 2 cycles at 0.5 µL/min flow rate and 20 second pauses. Wash was repeated twice in 500 µL of fresh Wash Buffer. The ethanol was dried from the resin bed by ejecting the plasmid DNA pipette tip columns in a vacuum adapter and a vacuum was applied that was capable of moving at least 4 Cubic Feet per Minute (CFM). The vacuum was applied for 5 minutes. The liquid handling robot reattached the plasmid DNA pipette tip columns and eluted the pure plasmid DNA by aspirating 170 µL Elution Buffer (10 mM Tris-HCl pH 8.5) and incubating it for 5 minutes. The plasmid was released by dispensing 170 µL into a microplate.

Example 4

Comparison of Pipette Tip Columns and Spin Columns

The pipette tip columns used in this example contained 80 µL of medium and were fitted with 105 µm pore size screen bottom frits. A side by side comparison with commercial spin columns was made using buffers listed in Table 7. *E. coli* was grown overnight in 1.4 mL medium in a 96-well deep-well plate. The results of three representative samples are shown in Table 5.

TABLE 7

| Buffers | |
|---|---|
| Buffer Name | Content |
| Resuspension buffer | 50 mM Tris-HCl pH 8.0, 10 mM EDTA, 100 ug/mL RNase A |
| Lysis buffer | 200 mM NaOH, 1% SDS |
| Neutralization buffer | 4.2M guanidine hydrochloride 0.9M Potassium acetate pH 4.5 |
| Equilibration buffer | water |
| Wash1 buffer | 5M guanidine hydrochloride 30% Ethanol, 10 mM TRIS-HCl pH 6.6 |
| Wash2 buffer | 10 mM TRIS-HCl pH 7.5, 80% Ethanol |
| Elution buffer | Water |

TABLE 8

Comparison of pipette tip columns and spin columns
Representative results from purification of plasmid performed with a commercial spin columns used with three sequential elutions (Spin C1, Spin C2 and Spin C3) and two types of pipette tip columns. E1, E2 and E3 refer to the recovery from three sequential elution aliquots, elutions 1 through 3.

| Column Name | A260 | Conc (ng/µL) | A260/A280 | Total µg | Combined total µg |
|---|---|---|---|---|---|
| Spin C1 (100 µL elution) | 0.86 | 43.05 | 1.78 | 4.30 | |
| Spin C2 (100 µL elution) | 0.19 | 9.6 | 1.63 | 0.96 | |
| Spin C3 (100 µL elution) | 0.14 | 7.05 | 1.10 | 0.70 | 5.97 |
| Pipette Tip [top frit] E1 (100 µL) | 1.12 | 56.2 | 1.97 | 5.62 | |
| Pipette Tip [top frit] E2 (100 µL) | 0.51 | 25.5 | 1.93 | 2.55 | |
| Pipette Tip [top frit] E3 (100 µL) | 0.28 | 14.25 | 1.73 | 1.42 | 9.59 |
| Pipette Tip [no top frit] E1 (100 µL) | 0.61 | 30.75 | 1.92 | 3.07 | |
| Pipette Tip [no top frit] E2 (100 µL) | 0.64 | 31.95 | 1.92 | 3.19 | |
| Pipette Tip no [top frit] E3 (100 µL) | 0.37 | 18.55 | 1.80 | 1.85 | 8.12 |

Example 5

Miniprep of *E. coli* Plasmid DNA from 96 Samples at a Time

Figure 4:
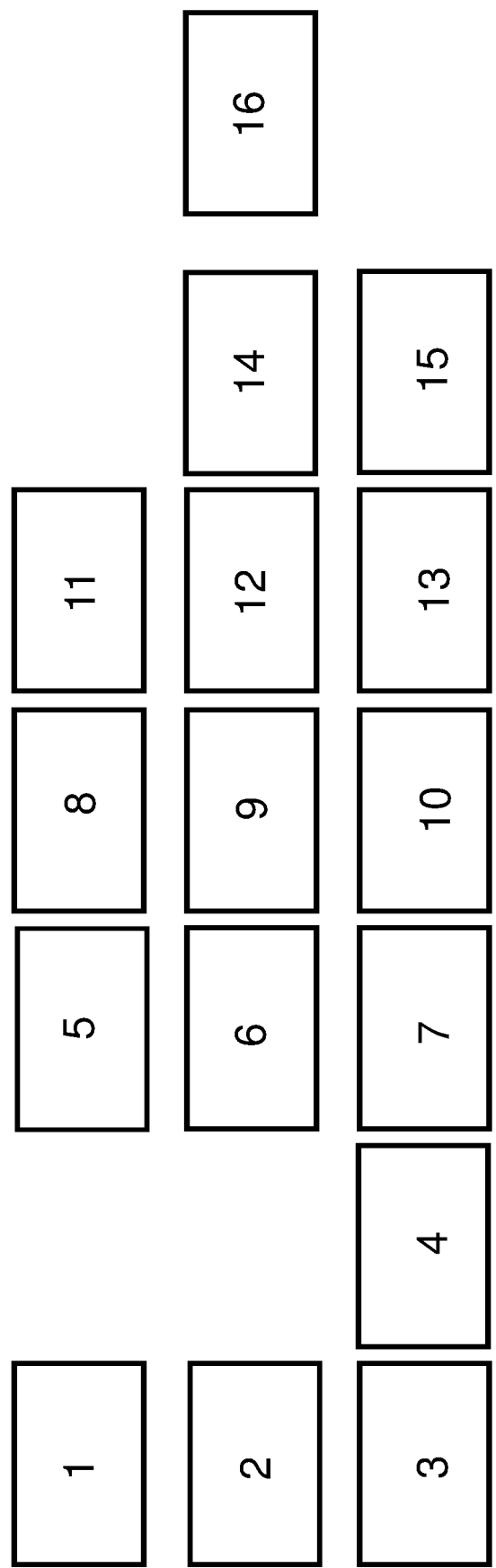
FIG. 4 depicts the layout of the deck of the Tecan Freedom Evo automated liquid handler.

Single colonies were inoculated into 1.4 ml rich medium (containing the appropriate antibiotic) in a 2-ml deep-well block and incubated at 37° C. and 300 rpm for 16 hours. The deep-well block was centrifuged and the medium was discarded. The plate was then transferred to a Tecan Freedom Evo liquid handler with the deck set up described as follows and shown in FIG. 4.

Positions 1 through 3 contain boxes of 200-μL pipette tips. Position 4 has a box of 96 pipette tip columns. In this example the pipette tip columns are constructed with a bottom frit only (pore size 105 μm) and filled with 80 μL of silica resin. Position 5 holds a 96-well plate filled with 250 μL, precipitation Buffer in each well. Positions 6 and 7 contain plates holding lysis and resuspension buffers, respectively. Positions 8, 11 and 12 contain buffers for wash 1, wash 2 and wash 3, respectively. In this procedure, wash 3 is the same solution as wash 2. Each of these is a deep-well block holding 500 μL of buffer. A deep-well block holding 300 μL Equilibration buffer is placed in position 9. The deep-well plate holding the cell pellets is placed at position 10. There is a UV-readable plate at position 13 to receive the purified plasmid DNA. Stations 14 and 15 can be used for drawing air through the pipette tip columns with vacuum and a UV plate reader resides at position 16.

The plate was processed as follows.
1. Resuspend cells. Transfer 150 ul resuspension buffer to cell pellet. 130 ul, 8-16 cycles, 10 ml/min.
2. Lyse cells. Add 150 uL of Lysis buffer to resuspended cells. 8 cycles of 180 μL at 10 ml/min with 2 sec pause.
3. Add 210 μL precipitation buffer. 8 cycles of 180 μL at 10 ml/min with 2 sec pause.
4. Attach pipette tip columns to the 96-channel head. Equilibrate the pipette tip columns. 2 cycles of 180 μL, 0.5 ml/min with 5 sec pause.
5. Capture
   a. Aspirate 200 μL air at 0.25 ml/min with 2 sec pause
   b. Submerge pipette tip column in unclarified lysate and expel 200 μL air at 0.25 ml/min with 2 sec pause. Particulates should float.
   c. Capture. 180 μL of unclarified lysate, 14 cycles at 0.25 ml/min with 20 sec pause.
6. Wash 1. 180 μL of wash buffer 1, 2 cycles at 0.5 ml/min with 10 sec pause.
7. Wash 2. 180 μL of wash buffer 2, 2 cycles at 0.5 ml/min with 10 sec pause.
8. Wash 3. 180 μL of wash buffer 2, 2 cycles at 0.5 ml/min with 10 sec pause.
9. Vacuum dry. Deposit tips to vacuum station and vacuum air through the tips for 5 min.
10. Elution
    a. Aspirate 70 μL of air
    b. Engage tips and aspirate 130 μL of elution buffer at 0.25 ml/min.
    c. Incubate 5 min.
    d. Expel 130 μL of purified plasmid at 0.25 ml/min.

TABLE 9

| Buffer Name | Content |
| --- | --- |
| Resuspension buffer | 50 mM Tris-HCl pH 8.0, 10 mM EDTA, 0.4 mg/mL RNase A |
| Lysis buffer | 200 mM NaOH, 2.5% SDS |
| Precipitation buffer | (A) 0.9M Potassium acetate pH 4.5 (B) 4.2M Guanidinium-HCl |
| Equilibration Solution | Water |
| Wash buffer | 100 mM TRIS-HCl pH 7.5, 65% Ethanol |
| Elution buffer | 10 mM Tris, pH 8.5 |

Example 6

Procedure for Midiprep of E. coli Plasmid DNA from 96 Samples at a Time

The buffers used in this example are listed in Table 9.
1) In 10 mL of LB or Agencourt Ale medium, inoculate a single colony.
2) Grow overnight. 37° C., 16 hours at 300 rpm.
3) Centrifuge for 25 minutes at 3000 rpm.
4) Discard the supernatant.
5) Resuspend pellet with 150 μl resuspension buffer.
6) Add 1 mL of lysis buffer. Mix thoroughly.
7) Add 1.4 mL of precipitation buffer. Mix thoroughly.
8) Attach pipette tip columns to the ME/MEA and equilibrate in 500 uL of equilibration solution. The columns contain a 300 μL bed in a 1 mL pipette tip (2 cycles at 0.5 ml/min).
9) Intake 1 mL air into the column at a flow rate of 0.5 ml/min.
10) Move the pipette tip column to the bottom of the precipitated sample.
11) Expel 1 mL of air at 10 ml/min.
12) Capture plasmid by performing 10-15 cycles (0.25 ml/min or 0.5 ml/min).
13) Five wash steps. Move the pipette tip columns into a deep well block containing 1 mL of wash buffer. 4 cycles (0.5-5 ml/min).
14) Air dry. Use vacuum pump. 5-15 minutes.
15) Move the pipette tip columns into the deep well block containing elution buffer.
16) Intake 1333 μl, wait 5 min and expel.

Example 7

Midiprep of E. coli Plasmid DNA Using a Combination of Back and Forth Flow and Gravity Flow.

In this example, the midiprep is performed as described in the preceding example except the wash and elution steps are done using gravity flow. The column is washed with 1 ml of buffer and the wash step is repeated 10-15 times. For the elution step, 1.2 mL of elution buffer is used.

Example 8

Midiprep of E. coli Plasmid DNA Using Gravity Flow.

In this example, the midiprep is performed as described in the preceding example except the capture step is performed using gravity flow.

Example 9

Extraction of DNA from Agarose Gel

The nucleic acids in this example are not limited to plasmid DNA. This procedure can be used to isolate nucleic acids of any type or size distribution that can be visualized on a gel. Agarose gel electrophoresis is the most common method for size separation and visualization of double stranded DNA. Agarose gels are used to separate DNA based on the mass (and thus, the length) of the DNA. Shorter DNA migrates farther through the gel compared to a long DNA. In practice, agarose gels are used to purify PCR products away from free primers, dNTPs, DNA polymerase and buffer components. The PCR product will migrate as a discreet band. Restriction digests of plasmids, for example, also result in discreet bands that can be purified by agarose gel. Discreet bands correspond to DNA of the same length. To utilize this separation as a pre-purification tool, the band corresponding to the DNA length of interest is excised from the gel using a scalpel or razor blade. The band is weighed and is placed into a microfuge tube. Three volumes of gel extraction buffer (50 mM MOPS pH 7.0, 1M NaCl, 15% (v/v) isopropanol) is added to the excised gel using the conversion 1 mg=1 µL. The tube is incubated at 50° C. for 10 minutes. The tube is vortexed every 2 to 3 minutes during this incubation. One volume of isopropanol is added to the tube.

A plasmid DNA pipette tip purification column is used to capture the DNA. The column is processed by the PhyNexus MEA personal purification instrument. The MEA engages the pipette tip column and equilibrates it with 2 cycles of back-and-forth flow in water using a flow rate of 0.5 mL/min and 20 second pauses at the end of each aspirate and dispense step. Next, the column captures the extracted DNA. This is accomplished using 4-20 cycles of back-and-forth flow at a flow rate of 0.25 mL/min and 20 second pauses at the end of each aspirate and dispense step. The columns are subject to a wash in 0.5 mL wash buffer (80% ethanol, 10 mM Tris-HCl pH 7.5). The wash is repeated in fresh buffer an additional two times. After washing, the pipette tip columns are transferred to a vacuum block and subject to 5 minutes of vacuuming to dry the columns to remove residual wash buffer components. The MEA next engages the pipette tip columns and aspirates 130 µL of water and incubates for 5 minutes. This is dispensed to release the plasmid DNA and a second elution is performed if necessary.

Example 10

Automated Purification of Bacterial Genomic DNA on the PhyNexus MEA
1. Grow bacterial cells in 25 to 50 mL Agencourt Ale in 250 mL shake flasks overnight at 37° C.
2. Aliquot cells (less than 1 ml per well) into 96-well, deep-well plates.
3. Lyse with 1000 µL Lysis Buffer (9 mM Tris, 0.55% SDS—final pH 9)
4. Mix by pipetting back/forth
5. Incubate 30 min at room temperature
6. Add 100 µL PL buffer (20 mM EDTA; 3.885 µg/µL RNaseA)
7. Mix by pipetting back/forth
8. Capture unidirectionally with assistance by vacuuming and agitation by engaging columns and executing quick back and forth pipetting. Capture: 500 µL of the lysate is taken up and dispensed on the top of the column. The vacuum is engaged for 30 seconds. The columns are engaged and quick (20 mL/min) back and forth pipetting of 500 µL volume is carried out to loosen the resin bed. The columns are disengaged back into the vacuum and vacuum for 30 seconds. This whole process is repeated two more times with the rest of the lysate.
9. Repeat until all lysate is processed through bed
10. Wash by cycling 5×1 mL WB(P)75 (100 mM Tris pH 7.5, 75% EtOH) with vacuuming for 30 seconds between each aliquot
11. Vacuum for 5 minutes to evaporate ethanol
12. Pump 280 µL EB(P) (10 mM Tris pH 8.5) back and forth for 5 cycles with pauses after intakes totaling 8 minutes.
The PhyNexus MEA method is described in detail below.
1. Resuspend cell pellet with 200 µL of resuspension buffer.
2. Add 1 mL of lysis buffer to resuspended sample.
3. Mix by aspirating and expelling 1 mL for 15 cycles at 13.3 mL/min.
4. Incubate sample at room temperature for 30 minutes.
5. Add 100 µL of PL buffer.
6. Mix by intaking and expelling 1 mL for 2 cycles at 13.3 mL/min.
7. The columns contain an 80 µL bed in a 1 mL pipette tip. Attach the pipette tip columns to the PhyNexus MEA and equilibrate in 500 µL of Equilibration solution (3 cycles at 13.3 mL/min).
8. Move columns into the drying station.
9. Intake 500 µL of sample and dispense the sample into the pipette tip columns.
10. Vacuum the columns for 30 seconds.
11. Engage the pipette tip columns onto pipette head and quickly intake and expel 500 µL of air for 5 cycles at 20 mL/min to loosen the resin bed.
12. Disengage the columns into the drying station.
13. Pass vacuum through the samples for 30 seconds.
14. Repeat steps 9 through 13 two more times.
15. Engage the pipette tip columns and move the columns to bottom of a well containing 1 mL of wash buffer.
16. Intake and expel 900 µL of the wash buffer at 1 mL/min for 2 cycles with 10 second pause after each intake and expel.
17. Disengage the columns into the drying station.
18. Pass air through the columns for 30 seconds.
19. Engage the pipette tip columns and move them to the bottom of a second well containing 1 mL of fresh wash buffer.
20. Intake and expel 900 µL of the wash buffer at 1 mL/min for 2 cycles with 10 second pause after each intake and expel.
21. Disengage the columns into the drying block.
22. Pass vacuum through the columns for 30 seconds.
23. Engage the pipette tip columns and move the columns to the bottom of a third well containing 1 mL of fresh wash buffer.
24. Intake and expel 900 µL of the wash buffer at 1 mL/min for 2 cycles with 10 second pause after each intake and expel.
25. Repeat steps 23 and 24 with two more 1 mL aliquots of fresh wash buffer.
26. Disengage the columns into the drying station.
27. Pass air through the columns for 5 minutes.
28. Engage the pipette tip columns and move them to the bottom of a well containing 280 µL of elution buffer.
29. Intake and expel 280 µL of the elution buffer into the well that contained the elution buffer. The flow rate is 0.5 mL/min for 2 cycles with 60 second pause after each intake.
30. Position the columns above the eluted sample surface and expel the remaining liquid from the column.

Example 11

Automated Purification of Worm DNA on the PhyNexus MEA
The method for purification of plasmid DNA from culture was modified for purification of genomic DNA from tissues. Generally, the modifications include the following changes
1. The preparation of sample. The tissues were prepared to generate a viscous supernatant by dissolving the solid tissues.
2. The precipitation procedure was eliminated because genomic DNA must stay in solution.
3. The capture of the sample was carried out by a single pass through the pipette tip column.

4. The stringency of the wash buffer was decreased to reduce loss of genomic DNA.

The following procedure was used for purification of genomic DNA from whole blood worms, *Chironomidae tetans*.

Procedure:
1) Transfer 20 mg sample to individual wells of a deep well plate.
2) Add 20 µL of 600 mU/mL Proteinase K to each sample.
3) Add 180 µL lysis buffer 1A (50 mM Tris-HCl pH 8.0, 100 mM NaCl, 3% SDS) to each sample. Note: lysis buffer 1B (100 mM Tris-HCl pH 8.0, 1.4 M NaCl, 20 mM EDTA, 3% CTAB (Cetyltrimethylammonium bromide)) can alternatively be used for lysis.
4) Incubate the deep well plate at 56° C. for 16 hours.
5) Add 5.7 µL of 0.07 mg/mL RNase A.
6) Incubate at room temperature for two minutes.
7) Add 200 µL of lysis buffer 2 (Qiagen ATL Buffer).
8) Incubate at 70° C. for ten minutes.
9) Add 200 µL of 100% ethanol to each sample.
10) Equilibrate pipette tip columns with 500 µL deionized water using two cycles of back-and-forth flow at a flow rate of 13 mL/min and 10 second pauses at the end of each aspirate and each dispense.
11) Capture genomic DNA by loading the sample to the top of the resin bed and flow through the pipette tip column by gravity or using vacuum.
12) Wash with 500 µL of wash buffer (10 mM Tris HCl pH 7.4, 70% ethanol) consisting of 2 cycles at a flow rate of 0.5 mL/minutes and 20 second pauses at the end of each aspirate and each dispense.
13) Repeat step 12 twice using fresh wash buffer.
14) Dry the ethanol from the resin bed by flowing 2.5 liters of air through the pipette tip column.
15) Elute the genomic DNA by aspirating 210 µL elution buffer (10 mM Tris HCl pH 8.5), incubating for 5 minutes and dispensing to release the purified DNA.

Example 12

Automated Purification of Mouse Tail DNA on the PhyNexus MEA

Mouse tail DNA is purified exactly as described above for worm DNA.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. An automated method for capturing plasmid DNA from bacterial cells, comprising:
(a) providing a bacterial culture comprised of bacterial cells in a growth medium, wherein the volume of the bacterial culture is at least 30 mL and wherein the concentration of bacterial cells is greater than $4 \times 10^9$ cells per mL growth medium;
(b) providing a filtration apparatus comprised of a filter and receptacle;
(c) providing at least one column, wherein the column has an open upper end and an open lower end, wherein the column contains a solid phase capable of plasmid DNA capture, and wherein the column is positioned in an automated apparatus;
(d) centrifuging the bacterial culture to obtain a cell pellet;
(e) decanting the growth medium;
(f) adding a resuspension buffer to the cell pellet;
(g) resuspending the cell pellet in the resuspension buffer to obtain a cell suspension;
(h) mixing a lysis buffer with the cell suspension to produce a cell lysate, wherein the cell lysate is comprised of plasmid DNA and cell debris;
(i) optionally, adding a precipitation buffer to the cell lysate;
(j) passing the cell lysate through the filter, using gravity, to produce a filtrate, the filtrate including the plasmid DNA and a portion of the cell debris; and
(k) passing the filtrate through the column in an automated fashion, wherein a portion of the plasmid DNA from the filtrate is captured on the solid phase within the column.

2. The method of claim 1, wherein at least two columns are provided and plasmid DNA is captured from at least two bacterial cultures processed in parallel.

3. The method of claim 1, wherein during step (j), a portion of the filtrate is removed from the filtration apparatus receptacle in an automated fashion and passed through the column.

4. The method of claim 1, wherein the lysis buffer is comprised of a surfactant, wherein the surfactant is SDS, and wherein the percentage of SDS in the lysis buffer is in the range of 1.1%-2.6%.

5. The method of claim 1, wherein the automated apparatus is comprised of a pumping means.

6. The method of claim 5, wherein the pumping means is a pipette, wherein the open upper end of the column is engaged with the pipette and wherein the filtrate is aspirated and expelled through the open lower end of column.

7. The method of claim 1, wherein the area of the filter is at least 3 cm$^2$.

8. The method of claim 1, wherein the volume of the bacterial culture is at least 90 mL.

9. The method of claim 1, wherein the volume of the bacterial culture is at least 1.5 L.

10. The method of claim 1, wherein the filter includes a screen comprising at least one of plastic, metal, nylon, glass, paper, or cloth.

11. An automated method for capturing plasmid DNA from bacterial cells, comprising:
(a) providing a bacterial culture comprised of bacterial cells in a growth medium, wherein the growth medium has a volume, and wherein the volume of the bacterial culture is at least 30 mL;
(b) providing a filtration apparatus comprised of a filter and receptacle;
(c) providing at least one column, wherein the column has an open upper end and an open lower end, wherein the column contains a solid phase capable of plasmid DNA capture, and wherein the column is positioned in an automated apparatus;
(d) centrifuging the bacterial culture to obtain a cell pellet, wherein the wet weight of the cell pellet is greater than 3 g/L of growth medium;
(e) decanting the growth medium;
(f) adding a resuspension buffer to the cell pellet;

(g) resuspending the cell pellet in the resuspension buffer to obtain a cell suspension;

(h) mixing a lysis buffer with the cell suspension to produce a cell lysate, wherein the cell lysate is comprised of plasmid DNA and cell debris;

(i) optionally, adding a precipitation buffer to the cell lysate;

(j) passing the cell lysate through the filter, using gravity, to produce a filtrate, the filtrate including a portion of the cell debris; and (k) passing the filtrate through the column in an automated fashion, wherein a portion of the plasmid DNA from the filtrate is captured on the solid phase within the column.

12. The method of claim 11, wherein following step (k), the column is washed and in an automated fashion and the plasmid DNA is eluted from the column in an automated fashion.

13. The method of claim 11, wherein at least two columns are provided and plasmid DNA is captured from at least two bacterial cultures processed in parallel.

14. The method of claim 11, wherein the volume of the bacterial culture is at least 90 mL and the wet weight of the cell pellet is greater than 4 g/L of growth medium.

15. The method of claim 14, wherein the volume of bacterial culture is at least 1.5 L and the wet weight of the cell pellet is greater than 4 g/L of growth medium.

16. The method of claim 11, wherein during step (j), a portion of the filtrate is removed from the filtration apparatus receptacle in an automated fashion and passed through the column.

17. The method of claim 11, wherein the area of the filter is at least 3 cm$^2$.

18. The method of claim 11, wherein the lysis buffer is comprised of a surfactant, wherein the surfactant is SDS, and wherein the percentage of SDS in the lysis buffer is in the range of 1.1%-2.6%.

* * * * *